US009981997B2

(12) United States Patent
Zhang et al.

(10) Patent No.: US 9,981,997 B2
(45) Date of Patent: May 29, 2018

(54) CHEMICAL REAGENTS FOR ATTACHING AFFINITY MOLECULES ON SURFACES

(71) Applicant: ARIZONA BOARD OF REGENTS ON BEHALF OF ARIZONA STATE UNIVERSITY, Scottsdale, AZ (US)

(72) Inventors: Peiming Zhang, Gilbert, AZ (US); Subhadip Senapati, Tempe, AZ (US); Saikat Manna, Tempe, AZ (US)

(73) Assignee: Arizona Board of Regents On Behalf of Arizona State University, Scottsdale, AZ (US)

( * ) Notice: Subject to any disclaimer, the term of this patent is extended or adjusted under 35 U.S.C. 154(b) by 25 days.

(21) Appl. No.: 15/033,004

(22) PCT Filed: Oct. 28, 2014

(86) PCT No.: PCT/US2014/062589
§ 371 (c)(1),
(2) Date: Apr. 28, 2016

(87) PCT Pub. No.: WO2015/065985
PCT Pub. Date: May 7, 2015

(65) Prior Publication Data
US 2016/0280723 A1  Sep. 29, 2016

Related U.S. Application Data

(60) Provisional application No. 61/898,177, filed on Oct. 31, 2013.

(51) Int. Cl.
| | |
|---|---|
| *C07C 317/00* | (2006.01) |
| *C07C 247/04* | (2006.01) |
| *C07F 7/18* | (2006.01) |
| *C07F 7/10* | (2006.01) |
| *C07C 315/00* | (2006.01) |
| *C07C 317/28* | (2006.01) |
| *C07F 7/04* | (2006.01) |
| *C07K 5/12* | (2006.01) |
| *C12N 15/115* | (2010.01) |
| *G01Q 70/18* | (2010.01) |
| *G01Q 60/42* | (2010.01) |

(52) U.S. Cl.
CPC .......... *C07F 7/1836* (2013.01); *C07C 315/00* (2013.01); *C07C 317/28* (2013.01); *C07F 7/045* (2013.01); *C07F 7/10* (2013.01); *C07F 7/1876* (2013.01); *C07K 5/126* (2013.01); *C12N 15/115* (2013.01); *G01Q 60/42* (2013.01); *G01Q 70/18* (2013.01); *C12N 2310/16* (2013.01); *C12N 2310/351* (2013.01); *C12N 2310/3517* (2013.01)

(58) Field of Classification Search
CPC .... C07F 7/1836; C07C 317/00; C07C 247/04
See application file for complete search history.

(56) References Cited

U.S. PATENT DOCUMENTS

| | | | |
|---|---|---|---|
| 5,879,436 A | 3/1999 | Kramer et al. | |
| 8,628,649 B2 | 1/2014 | Lindsay et al. | |
| 8,961,757 B2 | 2/2015 | Nuckolls et al. | |
| 8,968,540 B2 | 3/2015 | Reinhart et al. | |
| 9,140,682 B2 | 9/2015 | Lindsay et al. | |
| 9,274,430 B2 | 3/2016 | Gyarfas et al. | |
| 9,395,352 B2 | 7/2016 | Lindsay et al. | |
| 9,593,372 B2 | 3/2017 | Lindsay et al. | |
| 2011/0065164 A1 | 3/2011 | Gonzalez et al. | |
| 2011/0070735 A1 | 3/2011 | Shi | |
| 2013/0302901 A1 | 11/2013 | Lindsay et al. | |
| 2015/0010935 A1 | 1/2015 | Lindsay et al. | |
| 2015/0142327 A1 | 5/2015 | Ashcroft et al. | |
| 2015/0144506 A1 | 5/2015 | Lindsay et al. | |
| 2016/0018384 A1 | 1/2016 | Lindsay et al. | |
| 2016/0025702 A1 | 1/2016 | Lindsay et al. | |
| 2016/0097759 A1 | 4/2016 | Lindsay et al. | |
| 2016/0108002 A1 | 4/2016 | Zhang et al. | |
| 2016/0146828 A1 | 5/2016 | Lindsay et al. | |
| 2016/0258925 A1 | 9/2016 | Gyarfas et al. | |
| 2017/0003245 A1 | 1/2017 | Lindsay et al. | |
| 2017/0204066 A1 | 7/2017 | Lindsay et al. | |

FOREIGN PATENT DOCUMENTS

| | | |
|---|---|---|
| WO | 2012155007 | 11/2012 |
| WO | WO 2012/155007 A1 | 11/2012 |
| WO | 2015065985 | 5/2015 |

OTHER PUBLICATIONS

SENAPATI. Langmuir, 2013, 29, 14622-30.*
Jung et al., Direct quantitative analysis of HCV RNA by atomic force microscopy without labeling or amplification., Nucleic Acids Research, Dec. 2012, 40(22):11728-36.
Zhu et al., Nanomechanical recognition measurements of individual DNA molecules reveal epigenetic methylation patterns., Nature Nanotechnology, Nov. 2010, 5(11):788-91.
Raab et al., Antibody recognition imaging by force microscopy., Nature Biotechnology, Sep. 1999, 17(9):902-5.
Stroh et al., Single-molecule recognition imaging microscopy., PNAS, Aug. 2004, 101(34):12503-7.
Kienberger et al., Molecular recognition imaging and force spectroscopy of single biomolecules., Accounts of Chemical Research, Jan. 2006, 39(1):29-36.
Lin et al., Recognition Imaging with a DNA Aptamer., Biophysical Journal, Jun. 2006, 90(11):4236-8.
Wang et al., Single-epitope recognition imaging of native chromatin., Epigenetics & Chromatin, 2008, 1(1):10(9 pages).
Chtcheglova et al., Simultaneous topography and recognition imaging on endothelial cells., Journal of Molecular Recognition, 2011, 24(5):788-94.

(Continued)

*Primary Examiner* — Noble E Jarrell
(74) *Attorney, Agent, or Firm* — Cooley LLP; Brian P. Hopkins; Chun L. Yu

(57) ABSTRACT

Chemical linkage reagents, methods of making and method of using the same are provided. Chemical linkage reagents according to at least some of the embodiments of the present disclosure may be incorporated into or operatively-linked with affinity molecules for attachment to silicon oxide surfaces to, for example, measure interactions between an affinity molecule and its targeting biomolecules.

20 Claims, 12 Drawing Sheets

(56) References Cited

OTHER PUBLICATIONS

Creasey et al., Atomic force microscopy-based antibody recognition imaging of proteins in the pathological deposits in Pseudoexfoliation Syndrome., Ultramicroscopy, Jul. 2011, 111(8):1055-61.
Wang et al., High-Resolution Single-Molecule Recognition Imaging of the Molecular Details of Ricin—Aptamer Interaction., Journal of Physical Chemistry B, 2012, 116:5316-22.
Hinterdorfer et al., Poly(Ethylene Glycol): An Ideal Spacer for Molecular Recognition Force Microscopy/Spectroscopy., Single Molecules, 2000, 1(2):99-103.
Riener et al., Simple test system for single molecule recognition force microscopy., Analytics Chimica Acta, Mar. 2003, 479(1):59-75.
Hinterdorfer et al., Surface attachment of ligands and receptors for molecular recognition force microscopy., Colloids and Surfaces B: Biointerfaces, Feb. 2002, 23:115-23.
Ebner et al., A New, Simple Method for Linking of Antibodies to Atomic Force Microscopy Tips., Bioconjugate Chemistry, Jul. 2007, 18(4):1176-84.
Ebner et al., Comparison of different aminofunctionalization strategies for attachment of single antibodies to AFM cantilevers., Ultramicroscopy, 2007, 107:922-7.
Jauvert et al., Probing single molecule interactions by AFM using bio-functionalized dendritips., Sensors and Actuators B: Chemical, 2012, 168:436-41.
Johnson, Application Note: Attaching Antibodies to AFM Probes with the Sulfhydryl Reactive PEG Tether, NHS-PEG18-PDP., Agilent Technologies, 2007, 4 pages.
Kamruzzahan et al., Antibody linking to atomic force microscope tips via disulfide bond formation., Bioconjugate Chemistry, 2006, 17(6):1473-81.
Li et al., In situ Single Bio-Molecule Recognition by Atomic Force Microscopy Using Functionalized Tip., Proceedings of 2005 5th IEEE Conference on Nanotechnology, Jul. 2005, 121-4.
Limanskii, Functionalization of amino-modified probes for atomic force microscopy, Biophysics, Apr. 2006, 51 (2):186-95.
Riener et al., Heterobifunctional crosslinkers for tethering single ligand molecules to scanning probes., Analytica Chimica Acta, 2003, 497(1):101-14.
Wilding et al., Linking of sensor molecules with amino groups to amino-functionalized AFM tips., Bioconjugate Chemistry, Jun. 2011, 22(6):1239-48.
Limansky et al., Aminomodified Probes for Atomic Force Microscopy., Probe Microscopy, Jan. 2002, 2(3-4):227-34.
Vandenberg et al., Structure of 3-aminopropyl triethoxy silane on silicon oxide., Journal of Colloid and Interface Science, Nov. 1991, 147(1):103-18.
Guha Thakurta et al., Fabrication of dense, uniform aminosilane monolayers: A platform for protein or ligand immobilization., Fabrication of dense, uniform aminosilane monolayers: A platform for protein or ligand immobilization, Colloids and Surfaces A: Physiochem. Eng. Aspects Nov. 2012, 414:384-92.
Lyubchenko et al., AFM for analysis of structure and dynamics of DNA and protein-DNA complexes., Methods, Mar. 2009, 47(3):206-13.
Lyubchenko et al., Imaging of nucleic acids with atomic force microscopy., Methods, 2011, 54(2):274-83.
Lyubchenko et al. Chapter 21: Atomic Force Microscopy Imaging and Probing of DNA, Proteins, and Protein-DNA Complexes: Silatrane Surface Chemistry. Tom Moss and Benoît Leblanc (eds.). Methods in Molecular Biology, DNA-Protein Interactions, vol. 543, pp. 337-351, Mar. 16, 2009.
Senapati et al. Application of Catalyst-free Click Reactions in Attaching Affinity Molecules to Tips of Atomic Force Microscopy for Detection of Protein Biomarkers. Langmuir 29(47): pp. 1-22, Nov. 26, 2013.
International Search Report and Written Opinion, dated Mar. 10, 2015, for International Application No. PCT/US2014/062589.
McMahan et al., Use of aryl azide cross-linkers to investigate protein-protein interactions: an optimization of important conditions as applied to Escherichia coli RNA polymerase and localization of a sigma 70-alpha cross-link to the C- terminal region of alpha., Biochemistry, Oct. 1994, 33(40):12092-12099.
Ni et al., Structures of the Escherichia coli transcription activator and regulator of diauxie, XylR: An AraC DNA-binding family member with a LacI/GalR ligand-binding domain., Nucleic Acids Research, Feb. 2013, 41(3):1998-2008.
Silantranes et al., A review on their synthesis, structure, reactivity and applications., Chemical Society Reviews, Mar. 2011, 40(3):1791-1840.
Lopez-Jaramillo et al., Vinyl Sulfone: A Multi-Purpose Function in Proteomics, Integrative Proteomics (ed. Hon-Chiu Leung), 2012, pp. 201-326.
Shlyakhtenko et al., Silatrane-based surface chemistry for immobilization of DNA, protein-DNA complexes and other biological materials., Ultramicroscopy, 2003, 97(1):279-287.
Aldrich Chemistry, Chemical Ligation., ChemFiles, 2008, 8(1):1-20.
Jewett et al., Synthesis of a fluorogenic cyclooctyne activated by Cu-free click chemistry., Organic Letters, Nov. 2011, 13(22):5937-5939.
Berquand et al., Common Approaches to Tip Functionalization for AFM-Based Molecular Recognition Measurements., Bruker Nano Surfaces Business, 2010, pp. 1-6.
Wang et al., Glutaraldehyde modified mica: a new surface for atomic force microscopy of chromatin., Biophysics Journal, Dec. 2002, 83(6):3619-3625.
Loiseau et al., Multigram Synthesis of Well-Defined Extended Bifunctional Polyethylene Glycol (PEG) Chains., Journal of Organic Chemistry, Feb. 2004, 69(3):639-47.
Nguyen et al., Quantifying Water at the Organic Film/Hydroxylated Substrate Interface., Journal of Adhesion, 1995, 48(1-4):169-194.
Svedhem et al., Synthesis of a Series of Oligo(ethylene glycol)-Terminated Alkanethiol Amides Designed to Address Structure and Stability of Biosensing Interfaces., Journal of Organic Chemistry, 2001, 66(13):4494-4503.
Lee et al., Atomic force microscopy: Determination of unbinding force, off rate and energy barrier for protein-ligand interaction., Micron, 2007, 38(5):446-461.
Zhang et al., Chemical Reagents for Attaching Recognition Molecules on Surfaces., Arizona Technology Enterprises, 2014, 1 page.
Lyubchenko et al., Atomic force microscopy imaging and probing of DNA, proteins, and protein DNA complexes: silatrane surface chemistry., Methods in Molecular Biology, Mar. 2009, 543: 337-351.
Senapati et al., Application of catalyst-free click reactions in attaching affinity molecules to tips of atomic force microscopy for detection of protein biomarkers., Langmuir, Nov. 2013, 29(47):14622-30.
Deshpande et al., Multiplexed nucleic acid-based assays for molecular diagnostics of human disease., Expert Review of Molecular Diagnostics, 2012, 12(6):645-659.
Ong et al., Personalized medicine and pharmacogenetic biomarkers: progress in molecular oncology testing., Expert Review of Molecular Diagnostics, 2012, 12(6):593-602.
Ogino et al., How many molecular subtypes? Implications of the unique tumor principle in personalized medicine., Expert Review of Molecular Diagnostics, 2012, 12(6):621-628.
Zieba, Molecular tools for companion diagnostics., New Biotechnology, 2012, 29(6):634-40.
Giljohann et al., Drivers of biodiagnostic development., Nature, 2009, 462(7272):461-464.
Archakov et al., AFM fishing nanotechnology is the way to reverse the Avogadro number in proteomics., Proteomics, 2007, 7(1):4-9.
Zhang et al., Ultrasensitive assays for proteins., Analyst, 2007, 132:724-737.
Hu et al., Ultrasensitive, multiplexed detection of cancer biomarkers directly in serum by using a quantum dot-based microfluidic protein chip., ACS Nano, Jan. 2010, 4(1):488-94.
Zhang et al., Nanotube-based colorimetric probe for ultrasensitive detection of ataxia telangiectasia mutated protein., Analytical Chemistry, 2011, 83(23):9191-6.

(56) References Cited

OTHER PUBLICATIONS

Li et al., Fluorescence enhancement of silver nanoparticle hybrid probes and ultrasensitive detection of IgE., Analytical Chemistry, Dec. 2011, 83(23):8945-52.

He et al., Immunoliposome-PCR: a generic ultrasensitive quantitative antigen detection system., Journal of Nanobiotechnology, Jun. 2012, 10(1):(start p. 26, 17 pages).

Foote et al., Kinetic and Affinity Limits on Antibodies Produced During Immune Responses., Proc. Natl. Acad. Sci. USA, Feb. 1995, 92(5):1254-6.

Grebe et al., LC-MS/MS in the Clinical Laboratory—Where to From Here?, Clin. Biochem. Rev., Feb. 2011, 32 (1):5-31.

Ruppen-Canas et al., An improved quantitative mass spectrometry analysis of tumor specific mutant proteins at high sensitivity., Proteomics, May 2012, 12(9):1319-27.

Shi et al., Antibody-free, targeted mass-spectrometric approach for quantification of proteins at low picogram per milliliter levels in human plasma/serum., Proc. Natl. Acad. Sci. USA, Sep. 2012, 109(38):15395-15400.

Rissin et al., Single-molecule enzyme-linked immunosorbent assay detects serum proteins at subfemtomolar concentrations., Nature Biotechnology, Jun. 2010, 28(6):595-9.

Hansma, Surface biology of DNA by atomic force microscopy., Annual Review of Physical Chemistry, 2001, 52:71-92.

Oroudjev et al., Surface Biology: Analysis of Biomolecular Structure by Atomic Force Microscopy and Molecular Pulling., Nanobiotechnology—Concepts, Applications and Perspective (Eds. C.M. Niemeyer, C.A. Mirkin), John Wiley % Sons, 2004, pp. 387-403.

Heinisch et al., Atomic force microscopy—Looking at mechanosensors on the cell surface., Journal of Cell Science, 2012, 125(18):4189-4195.

Muller et al., Force probing surfaces of living cells to molecular resolution., Nature Chemical Biology, Jun. 2009, 5(6):383-90.

Ramachandran et al., Potential role of atomic force microscopy in systems biology., WIREs Syst. Biol. Med., 2011, 3(6):702-16.

Safenokva et al., Application of atomic force microscopy for characteristics of single intermolecular interactions., Biochemistry (Moscow), Dec. 2012, 77(13):1536-52.

Shi et al., Living cell study at the single-molecule and single-cell levels by atomic force microscopy., Nanomedicine, Oct. 2012, 7(10):1625-37.

Oddershede, Force probing of individual molecules inside the living cell is now a reality., Nature Chemical Biology, Nov. 2012, 8(11):879-86.

Florin et al. Adhesion forces between individual ligand-receptor pairs., Science, Apr. 1994, 264(5157):415-7.

Dammer et al., Specific antigen/antibody interactions measured by force microscopy., Biophysical Journal, May 1996, 70(5):2437-41.

Luckham et al., Direct measurement of recognition forces between proteins and membrane receptors., Faraday Discussions, 1999, 111:307-20.

Allen et al., The influence of epitope availability on atomic-force microscope studies of antigen-antibody interactions., Biochemical Journal, Jul. 1999, 341(1):173-8.

Avci et al., Comparison of antibody—antigen interactions on collagen measured by conventional immunological techniques and atomic force microscopy., Langmuir, Dec. 2004, 20(25):11053-63.

Tanaka et al., Discrimination of DNA mismatches by direct force measurement for identification of tuna species., Analytica Chimica Acta, Mar. 2006, 561(1-2):150-5.

Neuert et al., Dynamic force spectroscopy of the digoxigenin—antibody complex., Jan. 2006, FEBS Letters, 580(2):505-9.

Carvalho et al., Atomic Force Microscopy-Based Molecular Recognition of a Fibrinogen Receptor on Human Erythrocytes., ACS Nano, 2010, 4(8):4609-20.

Meng et al., Adhesion between peptides/antibodies and breast cancer cells., Journal of Applied Physics, Jun. 2010, 107(11):114301(1-7).

Zapotoczny et al., Atomic force microscopy-based molecular studies on the recognition of immunogenic chlorinated ovalbumin by macrophage receptors., Journal of Molecular Recognition, Feb. 2012, 25(2):82-8.

\* cited by examiner

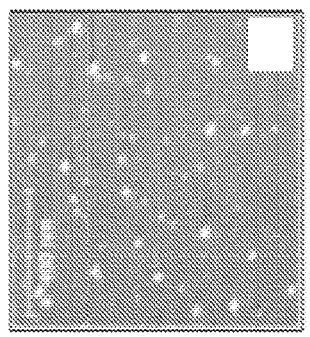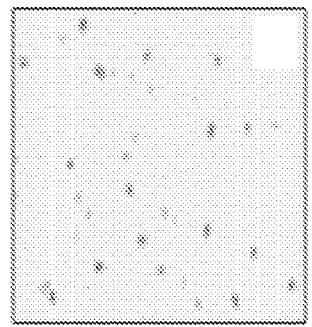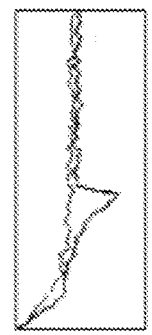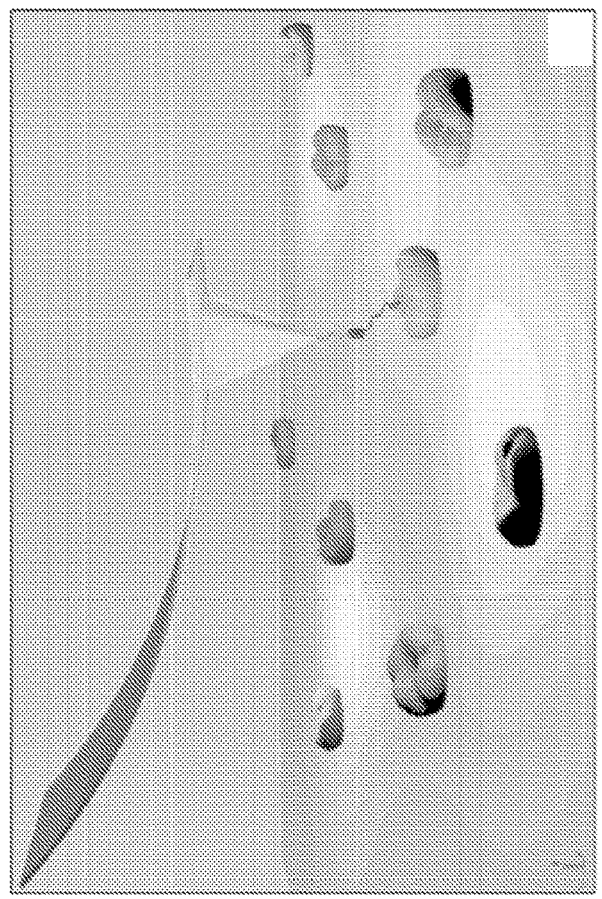

TBA-Thrombin Interaction

TBA-Thrombin Interaction

TBA-Thrombin Interaction

RGD-Integrin Interaction

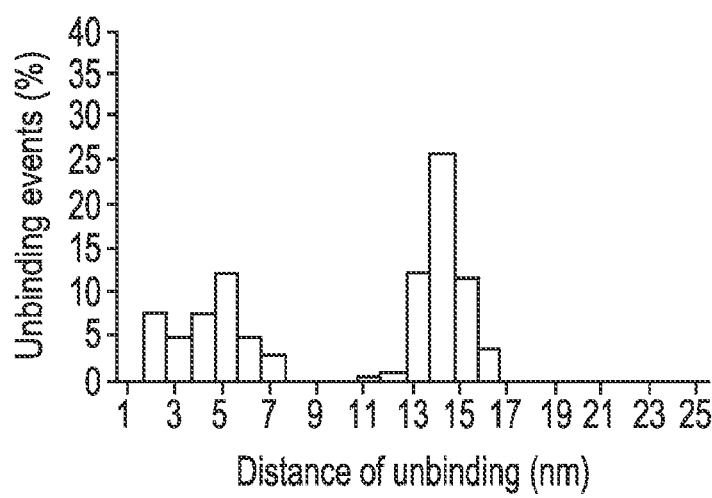
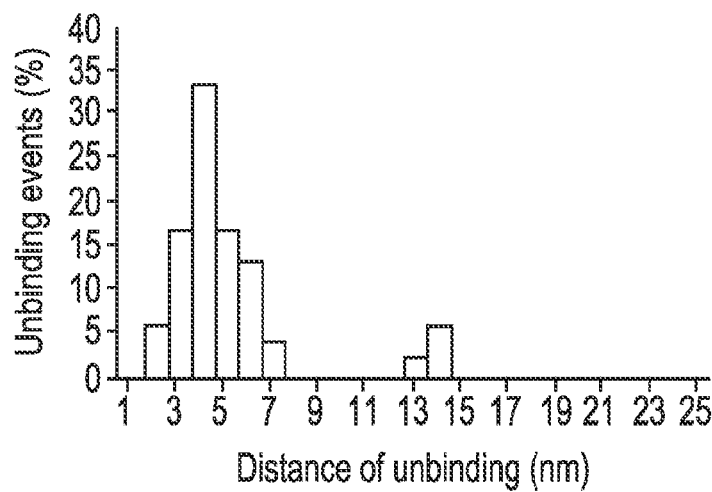

CHEMICAL REAGENTS FOR ATTACHING AFFINITY MOLECULES ON SURFACES

PRIORITY

This application is a U.S. national stage entry of PCT application No. PCT/US2014/062589, filed Oct. 28, 2014, which claims priority to U.S. Provisional Application No. 61/898,177 filed Oct. 31, 2013, titled "CHEMICAL REAGENTS FOR ATTACHING AFFINITY MOLECULES ON SURFACES", the entire disclosure of which is incorporated herein by reference.

GOVERNMENT SUPPORT

This invention was made with government support under U54 CA143862 awarded by the National Institutes of Health. The government has certain rights in the invention.

FIELD OF THE DISCLOSURE

This disclosure relates generally to the field of organic chemistry. Chemical linkage reagents, methods of making and method of using the same are provided. Chemical linkage reagents according to at least some of the embodiments of the present disclosure may be incorporated into or operatively-linked with affinity molecules for attachment to silicon oxide surfaces to, for example, measure interactions between an affinity molecule and its targeting biomolecules.

BACKGROUND

The human proteome is comprised of millions of proteins, many of which occur in minute concentrations below limits of detection (LOD) of current technologies such as ELISA, mass spectrometry and protein microarrays. Thus, there is a long felt need for a tool capable of directly detecting those disease relevant protein biomarkers present in low abundance without any additional manipulation such as post-assay signal amplification. Atomic Force Microscopy (AFM) has been envisioned as a means of nanodiagnostics due to its single molecule sensitivity. For its biological applications, robust experimental techniques incorporating well-designed chemistry and reliable bioassays are needed. Despite attempts by those in the field, prior to the development of the reagents described in this disclosure, an easy to operate, envirometally friendly chemical process had not been developed for use, especially in biological laboratories.

SUMMARY

Atomic Force Microscopy (AFM) has been used in studies of biological interactions. In this regard, AFM based force spectroscopy and recognition imaging are valuable tools for molecular diagnostics in clinics. These techniques involve attaching affinity molecules to AFM tips for detection of biomolecules. The attachment chemistry currently used on silicon tips involves multiple steps of reactions and moisture sensitive chemicals, such as (3-arninopropyl)triethoxysilane (APTES) and N-hydroxysuccinimide (NHS) ester, making the process difficult to operate in aqueous solutions. This disclosure provides a user-friendly protocol to functionalize the AFM tips with affinity molecules. The reactions of the protocols of this disclosure may be performed in aqueous solutions with high yields. According to protocols of the disclosure, two chemical reagents may be utilized: a molecular anchor that was synthesized by coupling cyclooctyne to silatrane for introduction of a chemically reactive function to AFM tips and a class of bi-functional polyethylene glycol linkers that harness two orthogonal click reactions, copper free alkyne-azide cycloaddition and thiol-vinylsulfone Michael addition, for attaching affinity molecules to AFM tips. The attachment chemistry was validated using silicon nitride (SiN) tips functionalized with anti-thrombin DNA aptamers and cyclo-RGD peptides to measure forces of unbinding these affinity molecules from their respective protein cognates human α-thrombin and human $\alpha_5\beta_1$-integrin immobilized on mica surfaces. The attachment chemistry of the disclosure has been applied to AFM based recognition imaging, allowing for detection of disease-relevant proteins with high sensitivity and specificity using silicon tips. These data and description provided in this disclosure demonstrate the suitability of the attachment chemistry for tethering affinity molecules to different types of AFM tips.

The disclosure provides methods for the synthesis of chemical linkage reagents, their incorporation to affinity molecules, and their attachment to silicon oxide surfaces for measuring interactions between affinity molecules and their targeting biomolecules.

The disclosure provides a compound of Formula I:
wherein:

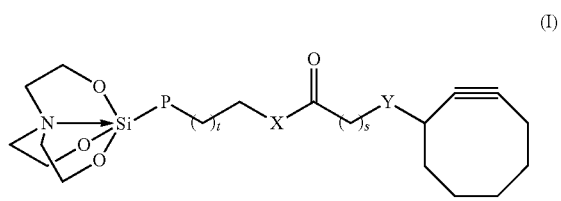

(I)

X is O, $CH_2$, NH or $NCH_3$;
Y is O, $CH_2$, NH or $NCH_3$;
P is $CH_2$ or O; and
s and t are each independently 0, 1, 2, 3, 4, or 5.

According to certain embodiments a compound according to Formula I, X is NH, Y is O, P is $CH_2$, t is 1, and s is 1. In one embodiment, the compound of Formula I may comprise

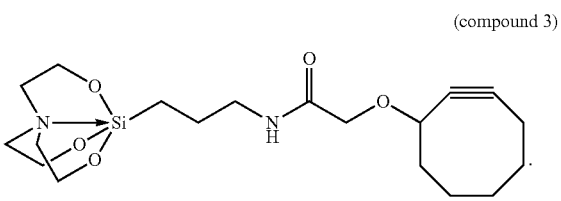

(compound 3)

According to certain embodiments of a compound according to Formula I, X is O, Y is O, P is O, t is 1, and s is 1. Moreover, the compound of Formula I may be a compound of Formula II:

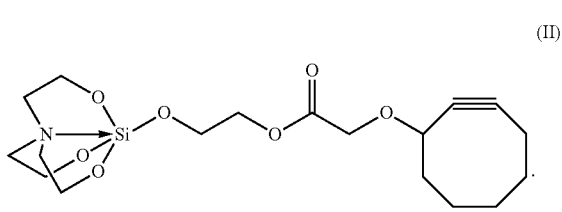

(II)

The disclosure provides a compound of Formula III:

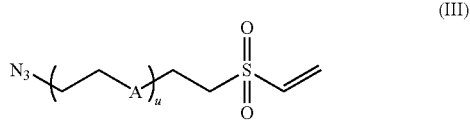

(III)

wherein:

A is $CH_2$ or O; and u is any integer ranging from 1 to 36.

According to certain embodiments of a compound according to Formula III, A is O. According to certain embodiments of a compound according to Formula III, u is 12. According to certain embodiments of a compound according to Formula III, u is 36.

According to certain embodiments of a compound according to Formula III, A is O and u is 12. A compound according to Formula III may be a compound of Formula IV:

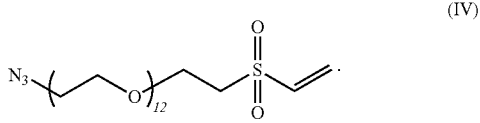

(IV)

According to certain embodiments of a compound according to Formula III, A is O and u is 36. A compound according to Formula III may be a compound of Formula V:

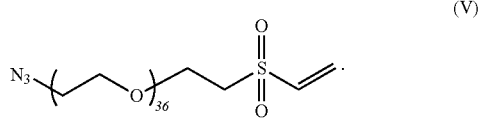

(V)

The disclosure provides a composition comprising a compound, at least one compound or one or more compounds of the disclosure. In certain embodiments of the compositions of the disclosure, a composition may comprise a molecular anchor, at least one molecular anchor, or one or more molecular anchor(s). In certain embodiments of the compositions of the disclosure, a composition may consist essentially of a molecular anchor, at least one molecular anchor, or one or more molecular anchor(s). In certain embodiments of the compositions of the disclosure, a composition may consist of a molecular anchor, at least one molecular anchor, or one or more molecular anchor(s). Exemplary molecular anchors of the disclosure may include, but are not limited to, a compound according to Formula I or Formula II, and compound 3.

In certain embodiments of the compositions of the disclosure, a composition may comprise a compound according to Formula I or II or compound 3, at least one compound according to Formula I or II or compound 3, or one or more compound(s) according to Formula I or II or compound 3. In certain embodiments of the compositions of the disclosure, a composition may consist essentially of a compound according to Formula I or II or compound 3, at least one compound according to Formula I or II or compound 3, or one or more compound(s) according to Formula I or II or compound 3. In certain embodiments of the compositions of the disclosure, a composition may consist of a compound according to Formula I or II or compound 3, at least one compound according to Formula I or II or compound 3, or one or more compound(s) according to Formula I or II or compound 3.

In certain embodiments of the compositions of the disclosure, a composition may comprise a compound according to Formula III, IV, or V, at least one compound according to Formula III, IV, or V, or one or more compound(s) according to Formula III, IV, or V. In certain embodiments of the compositions of the disclosure, a composition may consist essentially of a compound according to Formula III, IV, or V, at least one compound according to Formula III, IV, or V, or one or more compound(s) according to Formula III, IV, or V. In certain embodiments of the compositions of the disclosure, a composition may consist of a compound according to Formula III, IV, or V, at least one compound according to Formula III, IV, or V, or one or more compound(s) according to Formula III, IV, or V.

In certain embodiments of the compositions of the disclosure, a composition may comprise a compound according to Formula I, II, or compound 3, and a compound according to Formula III, IV, or V, at least one compound according to Formula I, II, or compound 3, and a compound according to Formula III, IV, or V, or one or more compound(s) according to Formula I, II, or compound 3, and a compound according to Formula III, IV, or V. In certain embodiments of the compositions of the disclosure, a composition may consist essentially of a compound according to Formula I, II, or compound 3, and a compound according to Formula II, IV, or V, at least one compound according to Formula I, II, or compound 3, and a compound according to Formula III, IV, or V, or one or more compound(s) according to Formula I, II, or compound 3, and a compound according to Formula III, IV, or V. In certain embodiments of the compositions of the disclosure, a composition may consist of a compound according to Formula I, II, or compound 3, and a compound according to Formula III, IV, or V, at least one compound according to Formula I, II, or compound 3, and a compound according to Formula III, IV, or V, or one or more compound(s) according to Formula I, II, or compound 3, and a compound according to Formula III, IV, or V.

In certain embodiments of the compositions of the disclosure, a composition may comprise a compound according to Formula I and III, IV, or V, at least one compound according to Formula I and III, IV, or V, or one or more compound(s) according to Formula I and III, IV, or V. In certain embodiments of the compositions of the disclosure, a composition may consist essentially of a compound according to Formula I and III, IV, or V, at least one compound according to Formula I and III, IV, or V, or one or more compound(s) according to Formula I and III, IV, or V. In certain embodiments of the compositions of the disclosure, a composition may consist of a compound according to Formula I and III, IV, or V, at least one compound according to Formula I and III, IV, or V, or one or more compound(s) according to Formula I and III, IV, or V.

In certain embodiments of the compositions of the disclosure, a composition may comprise a compound according to Formula II and III, IV, or V, at least one compound according to Formula II and III, IV, or V, or one or more compound(s) according to Formula II and III, IV, or V. In certain embodiments of the compositions of the disclosure, a composition may consist essentially of a compound according to Formula II and II, IV, or V, at least one compound according to Formula II and III, IV, or V, or one or more compound(s) according to Formula II and III, IV, or V. In certain embodiments of the compositions of the disclosure, a composition may consist of a compound according to Formula II and III, IV, or V, at least one compound according to Formula II and III, IV, or V, or one or more compound(s) according to Formula II and III, IV, or V.

In certain embodiments of the compositions of the disclosure, a composition may comprise a compound according to Formula III, IV, or V and compound 3, at least one compound according to Formula III, IV, or V and compound 3, or one or more compound(s) according to Formula III, IV, or V and compound 3. In certain embodiments of the compositions of the disclosure, a composition may consist essentially of a compound according to Formula III, IV, or V and compound 3, at least one compound according to Formula III, IV, or V and compound 3, or one or more compound(s) according to Formula III, IV, or V and compound 3. In certain embodiments of the compositions of the disclosure, a composition may consist of a compound according to Formula III, IV, or V and compound 3, at least one compound according to Formula III, IV, or V and compound 3, or one or more compound(s) according to Formula III, IV, or V and compound 3.

The disclosure provides a kit comprising, consisting essentially of, or consisting of a compound of the disclosure.

The disclosure provides a kit comprising, consisting essentially of or consisting of a composition of the disclosure.

The disclosure provides a method for preparing a compound according to Formula I comprising, contacting silatrane to a functionalized acid, wherein the contacting occurs in the presence of a coupling reagent. In certain embodiments of the methods of the disclosure, the contacting step further comprises an organic solvent. In certain embodiments of this method, the silatrane is 1-(3-aminopropyl)silatrane (APS). In certain embodiments of this method, the functionalized acid is 2-(cyclooct-2-yn-1-yloxy)acetic acid. In certain embodiments of this method, the coupling agent is 1-ethyl-3-(3-dimethylaminopropyl)carbodiimide (EDC). In certain embodiments of this method, the organic solvent is dichloromethane. In certain embodiments of this method, the compound according to Formula I, which may be (compound 3)

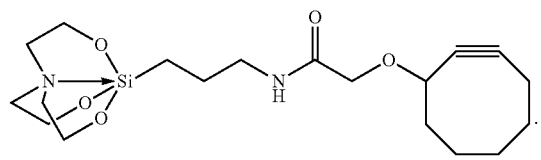

The disclosure provides a method of preparing a compound comprising compound 6a, comprising mixing hexatheylene glycol and

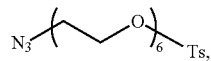
(compound 4)

wherein the mixing occurs in the presence of a first base to form

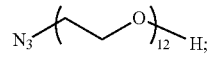
(compound 5)

and mixing divinyl sulfone,

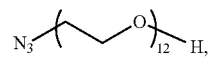
(compound 5)

and a second base, to form (compound 6a)

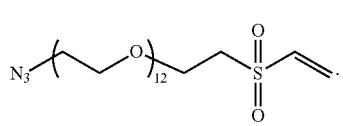

In certain embodiments of this method, the first base is sodium hydride. In certain embodiments of this method, the second base is potassium tert-butoxide.

The disclosure provides a method of preparing a compound comprising compound 6b, comprising mixing azido-dPEG36 alcohol glycol, divinyl sulfone, and a base. In certain embodiments of this method, the base is t-butoxide (e.g., potassium t-butoxide). The disclosure provides a method of attaching an affinity molecule to a molecular linker comprising contacting a nucleophilic moiety of the affinity molecule to a molecular linker in an aqueous medium. In certain embodiments of this method, the affinity molecule comprises, consists essentially of, or consists of a nucleic acid, a protein, a saccharide, a polysacharide, an organic molecule, or an inorganic molecule. In certain embodiments of this method, the nucleophilic moiety is a molecule comprising, consisting essentially of, or consisting of at least one of a nitrogen, a sulfur, or an oxygen atom. In certain embodiments of this method, the molecular linker comprises a compound according to Formula III. In certain embodiments of this method, the molecular linker comprises a compound according to Formula IV. In certain embodiments of this method, the molecular linker comprises a compound according to Formula V. In certain embodiments of this method, the nucleophilic moiety is a primary amine moiety. In certain embodiments of this method, the nucleophilic moiety is a thiol moiety. In certain embodiments of this method, the affinity molecule comprises a DNA aptamer. Exemplary DNA aptamers of the methods of the disclosure may comprise a thiol moiety. In certain embodiments of this method, the affinity molecule comprises a cyclic RGDfC peptide. Exemplary cyclic RGDfC peptides of the methods of the disclosure may comprise a thiol moiety.

BRIEF DESCRIPTION OF THE DRAWINGS

FIGS. 1A-D is a series of images illustrating an AFM tip with an affinity molecule tethered at its apex to specifically recognize its protein cognates immobilized on a substrate (A). Using contact mode, a force of the affinity molecule unbinding from its cognate can be determined by retracting the tip along the Z direction (B). By tapping the functionalized tip on the surface along the X to Y direction, topographic and recognition images can be generated (C, D). The affinity molecule may be, without limitation, a ligand, an antibody, and/or an aptamer.

FIGS. 14A-F is a series of graphs depicting various force measurements. (A) Solid line: a force-distance curve of a TBA functionalized tip retracting from a thrombin immobilized mica surface; red dotted line: a force-distance curve taken after blocking the TBA tip with thrombin; (B) A distance histogram of the ruptures taking place with the TBA functionalized tip retracting from the surface; (C) A distance histogram of the ruptures taking place after blocking the TBA tip with thrombin; (D) Solid line: a force-distance curve of a RGDfC functionalized tip retracting from a $\alpha_5\beta_1$ integrin immobilized mica surface; dotted line: a force-distance curve taken after blocking the RGDfC tip with integrin; (E) A distance histogram of the ruptures taking place with the RGD functionalized tip retracting from the surface; (F) A distance histogram of the ruptures taking place after blocking the RGD tip with integrin.

DETAILED DESCRIPTION

Figure 2:
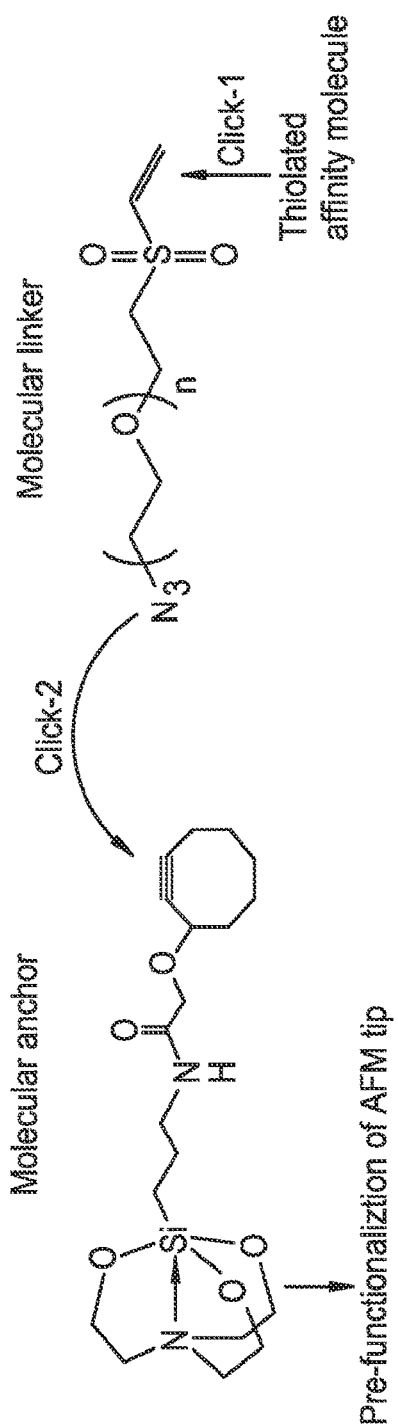
FIG. 2 is an illustration of a strategy to attach a biomolecule to an AFM tip functionalized with cyclooctyne through a heterobifunctional PEG linker by means of two orthogonal click reactions.

The human proteome consists of millions of proteins, many of which occur in minute concentrations below limits of detection (LOD) of current technologies such as ELISA, mass spectrometry and protein microarrays. Thus, there has been a long-felt and until the present disclosure, unmet need for an effective tool to detect those disease relevant protein biomarkers present in low abundance. AFM has been envisioned as a mean of nanodiagnostics due to its single molecule sensitivity. In combination with irreversible binding, AFM can reach a concentration sensitivity limit of $10^{-17}$ M. AFM has been exploited in the analysis of DNA, proteins and cells Moreover, AFM is useful for molecular analysis because it demonstrates chemical sensibility as well. As illustrated in FIG. 1, AFM is capable of "seeing and counting" target molecules when its tip is equipped with an affinity molecule. Affinity molecules may include, but are not limited to, proteins, DNA, peptides, drug molecules, ligands, receptors, carbohydrates, and metal complexes. For example, the interactions between antibody and antigen, ligand and receptor, DNA probe and target can be determined and characterized at a single molecule level by AFM force measurements, termed as Molecular Recognition Force Spectroscopy (MRFS). Also, AFM can probe individual biomolecules immobilized on a surface with an affinity molecule tethered to its tip, known as Recognition Imaging (RI). Both MRFS and RI may be used for identification and detection of protein biomarkers in a clinical setting, however, this combination is optimal when these techniques are robust because they are accompanied with well-designed chemistry and bioassays. Automated AFM-based force spectroscopy may facilitate the instrument operation. As demonstrated in this disclosure, facile attachment chemistry that works in aqueous solutions without any of organic solvents has been adapted to operate in biological laboratories and clinics.

A molecular linker may be employed to attach affinity molecules to AFM tips, which provides an advantage in distinguishing between specific and nonspecific interactions. Heterobifunctional poly[ethylene glycol] (PEG) may be used as a molecular linker When using heterobifunctional PEG as a molecular linker, the attachment generally follows a three-step workflow that begins with functionalizing an AFM tip with chemically reactive groups, and then attaches the PEG linker to the AFM tip, followed by reacting with an affinity reagent to finish the process.

(3-Arninopropyl)triethoxysilane (APTES) may be a reagent for amination of silicon tips, but it is notoriously problematic for forming uniform monolayers, especially when the reaction is carried out in a liquid phase. Chemical vapor deposition of APTES may be used to facilitate formation of uniform monolayers, for example, when the reaction is carried out in a liquid phase. This chemical vapor disposition may be facilitated by the use of an automated apparatus because, at least in part, the deposition chamber should be treated with argon to remove any trace amount of moisture. Preferably. APTES may be freshly redistilled before use.

The reaction of amine with NHS (N-Hydroxysuccinimide) ester may be used for tethering carboxylated PEG linkers to AFM tips. NHS ester is sensitive to moisture and may rapidly hydrolyze under basic conditions (above pH 8). In aqueous solutions, the pH, temperature, and reaction time may be optimized to minimize moisture and hydrolysis.

The disclosure provides a scheme for attaching affinity molecules to AFM tips based on click chemistry. Click chemistry may be characterized as a cyclization reaction of an alkyne and azide functionality (FIG. 2) but can also be a Michael addition of a vinyl sulfone with a nucleophile (e.g. amine or thiol moiety).

In certain embodiments of the disclosure, two orthogonal catalyst-free click reactions are performed for the attachment of affinity molecules to silicon tips. First, a molecular anchor may be synthesized by coupling cyclooctyne to silatrane for the introduction of an alkyne function to the silicon tip. The silatrane moiety reacts with silanol on silicon surfaces to form a monolayer in aqueous solution. Silatrane may be less reactive than alkoxysilanes and resistant to polymerization at a neutral pH. 1-(3-aminopropyl)silatrane (APS) may be used as a substitute of APTES in functionalizing AFM tips and mica surfaces. The ring strained cyclooctyne promotes the alkyne-azide reaction without any copper catalyst. An azido-PEG-vinyl sulfone linker may be prepared for click attachment.

In certain embodiments of the disclosure, thiolated oligonucleotide aptamers and affinity peptides may be attached to AFM tips. The reaction of vinyl sulfone with thiol in aqueous solution forms another category of click chemistry in bioconjugation, which may be used for the labeling of proteins and proteomes. The first click involves using the reaction of vinyl sulfone with thiol in aqueous solution to connect the thiolated affinity molecule to the linker as illustrated in, for example, in FIG. 2. The second click (azide to alkyne) may finish the process of the attachment. These two click reactions are orthogonal meaning that cross talk between these reactions is minimized.

The disclosure provides a scheme to attach affinity molecules to AFM tips for force spectroscopy and recognition imaging, based on two orthogonal click chemistries: catalyst free azide-alkyne cycloaddition and thiol-vinyl sulfone Michael addition. Reactions of the disclosure can be carried out in aqueous solutions without the use of organic solvents.

Two reagents were synthesized for implementation in the schemes and reactions of the disclosure. One reagent is an APS derivative of cyclooctyne for introduction of a chemically reactive group to AFM tips. The silatrane chemistry allows for the formation of a uniform monolayer in aqueous solution, which is particularly useful when the chemical is not volatile and the vapor deposition would not work. The operation is more convenient compared to the vapor deposition technique and the resulting surface is highly reproducible. Another reagent is a heterobifunctional linker "azido-PEG-vinyl sulfone". This heterobifunctional linker works for both AFM based force measurement and recognition imaging. The attachment process is easy to follow since there are no special requirements for the chemical reactions. With an increasing number of affinity oligonucleotides and peptides, these synthetic reagents may be used to detect more and more proteins. Incorporating thiol to peptides and oligonucleotides may be accomplished by custom synthesis, and, therefore, the attachment method of the disclosure is applicable to a broad range of affinity molecules.

EXAMPLES

Example 1: General Procedures

Chemicals were purchased from commercial suppliers (Sigma-Aldrich, Fluka, Santa Cruz Biotechnology, Alfa Aesar). Anhydrous organic solvents were Sure/Seal™ from Aldrich. Thrombin aptamers were custom synthesized by IDT (Integrated DNA Technologies) and human a thrombin was purchased from Abeam, Azido-dPEG® 36-alcohol was purchased from Quanta Biodesign, human α5β1 integrin from YO Proteins AB (Sweden), cylco(RGDfK) and cyclo (RGDfC) from Peptides international. All the synthetic reactions were carried out under nitrogen atmosphere. Thin layer chromatography (TLC) was used to monitor progress of organic reactions. An automated flash chromatography system (CombiFlash Rf, Teledyne Isco, Inc.) was used to separate the organic compounds with silica gel columns. FTIR data were collected using Thermo Scientific Nicole™ 6700 FT-IR spectrometer. The HPLC purification was carried out in Agilent 1100 series equipped with a UV detector and a fraction collector. Proton NMR($^1$H) spectra were recorded on a Varian 400 MHz instrument. $^1$H chemical shifts were referenced relative to the residual solvent peak (such as CDCl$_3$: $\delta_H$=7.24 ppm). MALDI-TOF analysis was performed on Voyager-DE STR instrument. Water was from Millipore's Milli-Q water purification system with a real time monitor of total of carbon (TOC) connected to a BioPak Polisher to remove biological contaminates. TOC level is strictly maintained below 5 ppb and resistivity at 18.2 MΩ×cm.

Example 2: Synthesis of N-(3-(silatranyl)propyl)-2-(cyclooct-2-yn-1-yloxy)acetamide (3)

EDC (115 mg, 0.6 mmol) was added to a solution of 2-(cyclooct-2-yn-1-yloxy)acetic acid (100 mg, 0.5 mmol) in anhydrous dichloromethane (2 mL), and the solution was stirred for 30 mins, followed by the addition of APS (140 mg, 0.6 mmol). After 3 hours, the reaction was stopped by rotary evaporation. The crude product was purified by flash chromatography in a silica gel column using a gradient of methanol (0-5% over 3 h) in dichloromethane to give a white solid (130 mg, 60%). $^1$H NMR (400 MHz, CDCl$_3$): δ=0.4-0.44 (m, 2H), 1.15-2.25 (m, 10H), 1.58-1.64 (m, 2H), 2.79

(t, 6H, J=6 Hz), 3.24 (m, 2H), 3.74 (t, 6H, J=6 Hz), 3.81 (d, 1H, J=15.2 Hz), 4.0 (d, 1H, J=15.2 Hz), 4.2 (t, 1H), 6.65 (s, 1H, broad); $^{13}$C NMR (50 MHz, CDCl$_3$): δ=13.2, 20.6, 24.9, 26.2, 29.6, 34.2, 41.8, 42.1, 51.1, 57.7, 68.5, 73.0, 91.5, 101.3, 169.1. HRMS (FAB): r/z (M+H) calculated for $C_{19}H_{32+1}N_2O_5Si$: 397.2158. found: 397.2159. With respect to nomenclature, to avoid excessive use of long series of numbers, a mathematical shorthand for expressing arithmentic progressions is used to denote the positions of oxygen atoms in the elongated PEG chains, as proposed by Loiseau et al. (J. Org. Chem., 2004, 69, 639-647).

Example 3: Synthesis of 35-azido-3n$_{33}^3$-undecaoxa-pentatriacontan-1-ol (5)

Sodium hydride (0.71 g, 29.5 mmol) was added to a solution of hexaethylene glycol (6.42 g, 22.7 mmol) in anhydrous THF (40 mL) with stirring at 0° C. to which a solution of compound 4 (3.5 g, 7.5 mmol) in anhydrous THF (20 mL) was added after 1 h. The mixture was allowed to warm to room temperature, stirred for another 15 hours. The reaction was stopped by dropwise adding methanol (5 mL). After removing the solvent, the crude product was purified by flash chromatography in a silica gel column using a gradient of methanol (0-5% over 4 h) in dicholoromethane. Compound 5 was obtained as a colorless liquid (3.1 g, 71%). $^1$H NMR (400 MHz, CDCl$_3$): δ=2.7 (s, 1H, broad), 3.34 (t, 2H, J=4.8 Hz), 3.55-3.69 (m, 46H); HRMS (FAB): m/z (M+H) calculated for $C_{24}H_{49+1}N_3O_{12}$: 572.3395. found: 572.3391.

Example 4: Synthesis of 1-Azido-35-(2-(vinylsulfonyl)ethoxy)-3n$_{33}^3$-undecaoxapentatriacontane (6a)

To a solution of 5 (100 mg, 0.18 mmol) in anhydrous THF (2 mL), divinyl sulfone (180 μL, 1.8 mmol) was added with stirring, followed by the addition of potassium t-butoxide (23 mg, 0.2 mmol). The reaction was monitored by thin layer chromatography (TLC). Within one hour, the starting material was consumed and a less polar spot observed on the TLC plate. The reaction mixture was filtered, concentrated, and purified by flash chromatography in a silica gel column using 0-4% gradient (over 4 hours) of methanol in dicholoromethane to furnish compound 6a as a colorless liquid (77 mg, 64%). $^1$H NMR (400 MHz, CDCl$_3$): δ=3.24 (t, 2H, J=5.2 Hz), 3.36 (t, 2H, J=5.2 Hz), 3.6-3.87 (in, 46H), 3.88 (t, 2H, J=5.2 Hz), 6.06 (d, 1H, J=9.6 Hz), 6.37 (d, 1H, J=16.8 Hz), 6.8 (dd, 1H, J=16.8 Hz and 10 Hz); $^{13}$C NMR (50 MHz, CDCl$_3$): characteristic peaks for PEG were observed. Two characteristic peaks for carbon atoms of vinyl sulfone was observed at δ=126.68, 137.99; HRMS (FAB): m/z (M+H) calculated for $C_{28}H_{55+1}N_3O_{12}S$: 690.3483. found: 690.3469.

Example 5: Synthesis of 1-Azido-35-(2-(vinylsulfonyl)ethoxy)-3n$_{105}^3$-pentatricontaoxaheptahectane (6b)

To a solution of Azido-dPEG® 36-alcohol (50 mg, 0.03 mmol) in anhydrous THF (I mL), divinyl sulfone (36 mg, 0.3 mmol) was added with stirring, followed by the addition of potassium t-butoxide (4 mg, 0.035 mmol). The reaction was monitored by thin layer chromatography (TLC). Within one hour, the starting material was consumed and a less polar spot observed on the TLC plate. The reaction mixture was filtered, concentrated, and purified by flash chromatography in a silica gel column using 0-4% gradient of methanol in dicholoromethane. The product 6b was separated as a white solid (33 mg, 61%). $^1$H NMR (400 MHz, CDCl$_3$): δ=3.26 (t, 2H, J=5.6 Hz), 3.39 (t, 2H, J=5.6 Hz), 3.5-3.7 (m, 142H), 3.9 (t, 2H, J=5.6 Hz), 6.09 (d, 1H, J=10 Hz), 6.39 (d, 1H, J=16.4 Hz), 6.82 (dd, 1H, J=10 Hz and 16.4 Hz); $^{13}$C NMR (50 MHz, CDCl$_3$): characteristic peaks for PEG were observed. Two characteristic peaks for carbon atoms of vinyl sulfone was observed at δ=128.7, 137.9; MALDI MS: m/z (M–H+ Na) calculated for $C_{76}H_{151-1}N_3O_{38}SNa$: 1769.0651. found: 1769.2117.

Example 6: Reactions of DNA Aptamers with Molecular Linkers

A solution (20 μL, 10 mM) of Thrombin-binding DNA aptamer 5'-GGTTGGTGTGGTTGG with a disulfide linker at 3'-end (IDT code: 3ThioMC3-D) in 0.1 M phosphate buffer (pH 8.0) was treated with TCEP (5 μL, 170 mM in 0.1 M TEAA buffer, pH 7.0). After 3 h, the reaction mixture was passed through a size-exclusion G-25 column (GE Healthcare) to remove small thiol molecules. The G-25 column was prepared following the protocol described by the manufacturers. First, the storage buffer was removed by centrifugation (1 min, 735×g). Then the column was rehydrated again with double distilled water, followed by centrifugation (1 min, 735×g). Finally, the reaction mixture was added to the column, followed by centrifugation (2 min, 735×g). The eluted solution containing thiol-functionalized aptamers (~25 μL) was then added to a solution of PEG linker 6a in 0.1 M phosphate buffer, pH 8.0 (20 μL, 50 mM). The reaction was finished in three hours, monitored by MALDI-TOF mass spectrometry. The product D-1a was purified using reverse phase HPLC with a Zorbax Eclipse Plus C18 column (4.6×150 mm, particle size 5 μm) with a gradient of 0% to 70% over a period of 25 mins (solvent A: a 0.1 M TEAA buffer, pH 7.0; solvent B: acetonitrile). The product has retention time of 17.4 min (with ~95% conversion). MALDI-TOF Mass: m/z (M+H) calculated for D-1a: 5570.51. found: 5571.63. After collecting the product using HPLC, the fraction was lyophilized to get the pure product.

D-1b was synthesized in the same way and purified by HPLC with retention time of 17.1 min (with conversion ~89%/). MALDI-MS: m/z (M+H) calculated for D-1b: 6649.23. found: 6650.37. After HPLC purification, the collected fraction was lyophilized.

Example 7: Reaction of Cyclo-RGD with Molecular Linkers (P-1b)

A solution of cyclo(RGDfC) (4 mM, 10 μL) in a phosphate buffer (0.1 M, pH 8.0) is mixed with 6b (4 mM, 10 μL) dissolved in phosphate buffer (0.1 M, pH 8.0). The reaction was stirred for three hours at room temperature, monitored by MALDI mass spectrometry for its completion. The conversion was 99.5%, determined by HPLC analysis. The product was purified by HPLC using a Zorbax Eclipse Plus C18 column (4.6×150 mm, particle size 5 μm) under a gradient of 20% to 70% over a period of 25 mins (Solvent A: 0.1% trifluoroacetic acid in de-ionized water; Solvent B: 0.09% trifluoroacetic acid in 80:20 acetonitrile: De-ionized Water; injection volume: 14 μL), monitored with a UV detector at a wavelength of 230 nm. The conjugate P-1b was eluted out at retention time of 17 min. MALDI-MS: m/z (M+H) calculated for P-1b: 2325.72. found: 2325.81.

P-1a was prepared in the same way as P-1b, purified by RP-HPLC, and characterized by MALDI-MS. MALDI-MS: m/z (M+H) calculated for P-1a: 1268.57. found: 1268.49. The conversion of peptide to its conjugate was quantitative. Both P-1a and P-1b fractions were lyophilized after HPLC purification.

Example 8: Functionalization of Silicon Substrates

Figure 12:
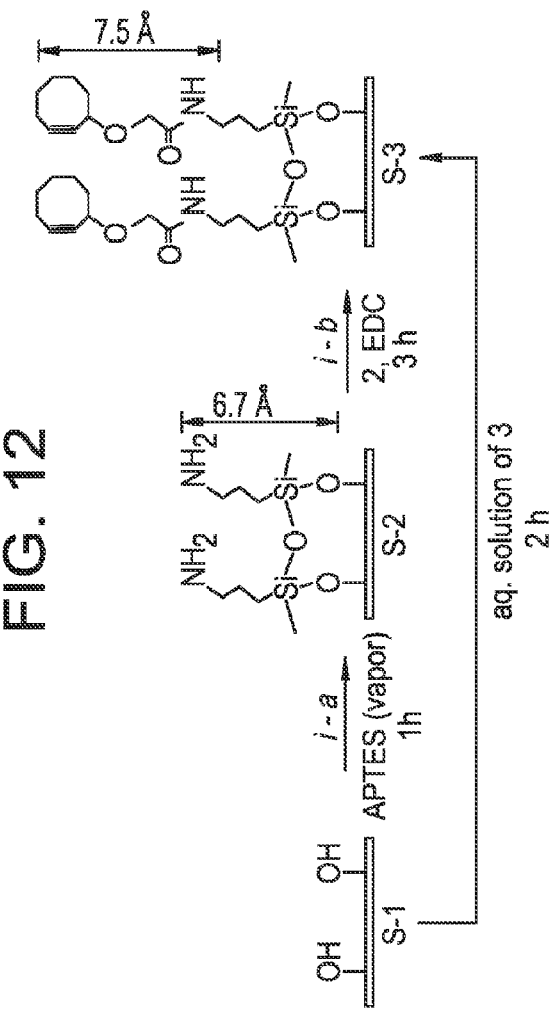
FIG. 12 is an illustration of an exemplary method to attach an anchor molecule to an ATM tip (functionalization of the silicon oxide surface): (i-a) chemical vapor deposition of APTES; (i-b) coupling of compound 2 to the APTES surface in DCM; (ii) reacting with compound 3 in an aqueous solution. Estimated molecular lengths determined using ChemDraw 3D.

Reactions i-a and i-b in FIG. 12:
A silicon substrate (1×1 cm2) was cleaned thoroughly with ethanol, dried by nitrogen, and then treated with oxygen plasma for two minutes using Harrick Plasma Cleaner (medium power). APTES was deposited on the substrate using a vapor deposition method (H. Wang, et al. Biophys. J., 2002, 83, 3619-3625). The aminated substrate was immersed in a solution of compound 2 (1 mg/mL). NHS/EDC (1 mg each) and triethyl amine (5 μL) in dry dicholoromethane. After three hours, the substrates were taken out and rinsed with dry dichloromethane (twice) followed by ethanol (twice) and dried with argon.

Reaction ii in FIG. 12:
A silicon substrate (1×1 cm2) was cleaned as described with respect to reactions 1-a nd 1-b, and then immersed in an aq. solution of silatrane derivative 3 (50 mM). After one hour, the substrates were taken out and rinsed five times with deionized water and dried with argon.

Example 9: Characterization of Monolayers

Contact angles were measured using Kruss EasyDrop. For the measurement, 2 μL of water droplets were deposited on different positions of a substrate placed on the sample plate and contact angles were measured in the video window of manufacturer's DSA software. Thicknesses of the monolayers were measured using Gaertner Scientific Corporation ellipsometer. For the thickness calculation, the refractive indices of both silicon oxide layers and organic layers were assumed to be 1.46 (T. Nguyen et al. J. Adhesion, 1995, 48, 169-194). Five different arbitrary positions on the substrate were chosen and the average value was taken. The thickness of the monolayer was determined by subtracting the silicon oxide thickness from the measured one.

Example 10: Reaction of Fluorescent Dye Labeled Azido-TBA on a Monolayer

Figure 17A:
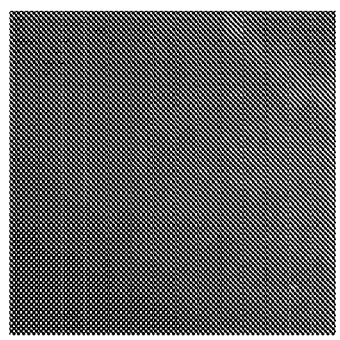
FIGS. 17A-B is a pair of images depicting (A) Fluorescence image of Surface A due to possible click reaction (cyclooctyne-azide); (B) fluorescence image of Surface B, a negative control.
Figure 17B:
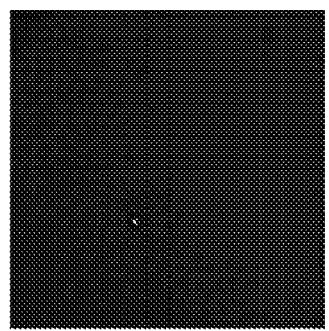

Oligonucleotide 5'-GGTTGGTGTGGTTGG with fluorescent tag (6-Carboxyfluorescein) at 5'-end and disulphide linker at 3'-end (IDT code: 3ThioMC3-D) was functionalized with an azide group exactly in the same way as for D-1a using linker 6a. MALDI-MS: m/z (M+H) calculated for azide functionalized fluorescent aptamer: 6101.04. found: 6102.17. The azide functionalized fluorescent aptamer was added to the cyclooctyne functionalized surface (FIG. 17A); meanwhile, another cyclooctyne functionalized surface (FIG. 17B) was treated with the fluorescent aptamer containing disulfide at the 3'-end. After one hour, both of the surfaces were washed thoroughly using phosphate buffer (0.1 M, pH 7.4). Fluorescence images were taken using a Zeiss LSM 510 Meta confocal microscope. As shown in FIGS. 17A-17B, the fluorescence intensity on surface A was four times time stronger than that on surface B.

Figure 3:
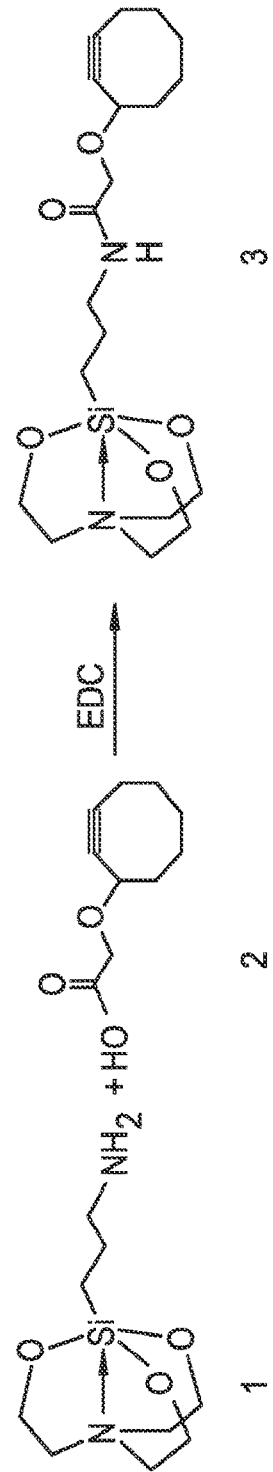
FIG. 3 is an illustration of a synthesis of N-(3-(silatranyl)propyl)-2-(cyclooct-2-yn-1-yloxy)acetamide.

Example 11: Synthesis in FIG. 3

Figure 4:
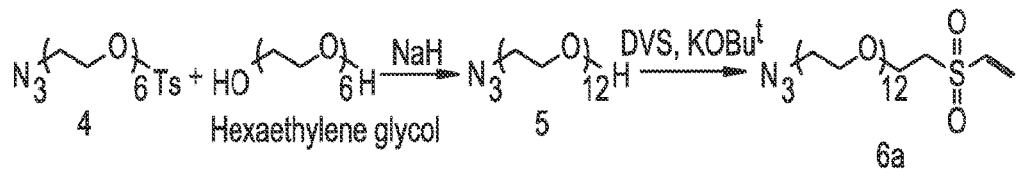
FIG. 4 is an illustration of a synthesis of a heterobifuntional PEG with 12 ethylene oxide units.
Figure 5:
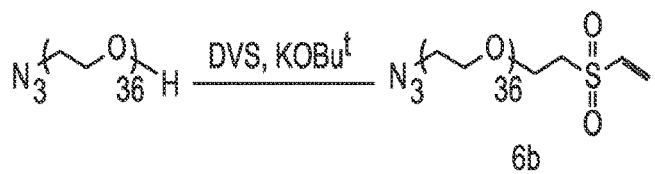
FIG. 5 is an illustration of a synthesis of a heterobifuntional PEG with 36 ethylene oxide units.
Figure 10A:
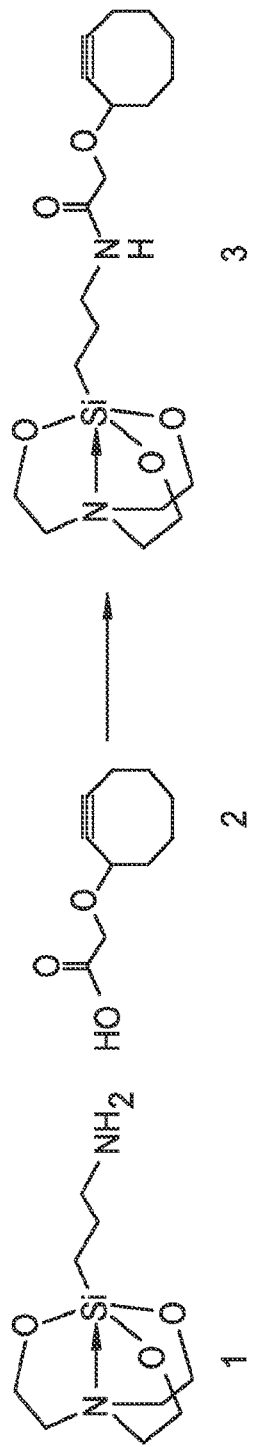
FIGS. 10A-C is a series of illustrations of: A. the synthesis of N-(3-(silatranyl)propyl)-2-(cyclooct-2-yn-1-yloxy)acetamide (3); B. the synthesis of 6a, a heterobifuntional PEG linker with 12 ethylene oxide units; C. the synthesis of 6b, a heterobifuntional PEG with 36 ethylene oxide units.
Figure 10B:
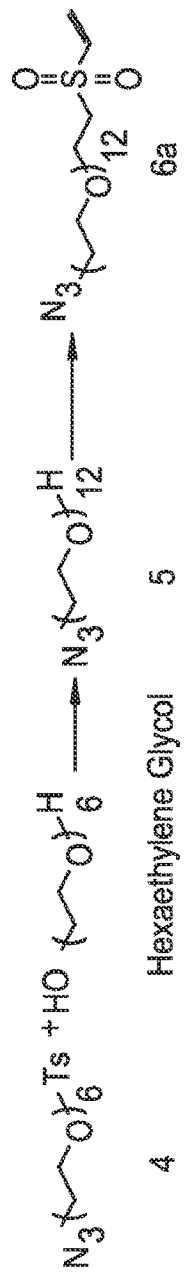
Figure 10C:
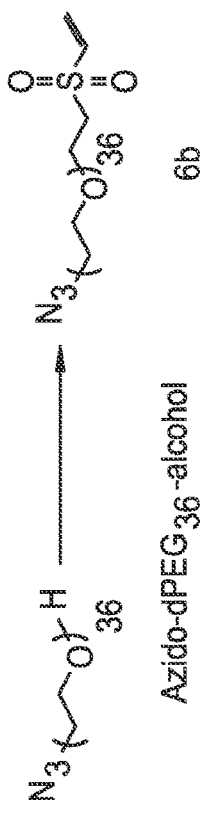
Figure 11:
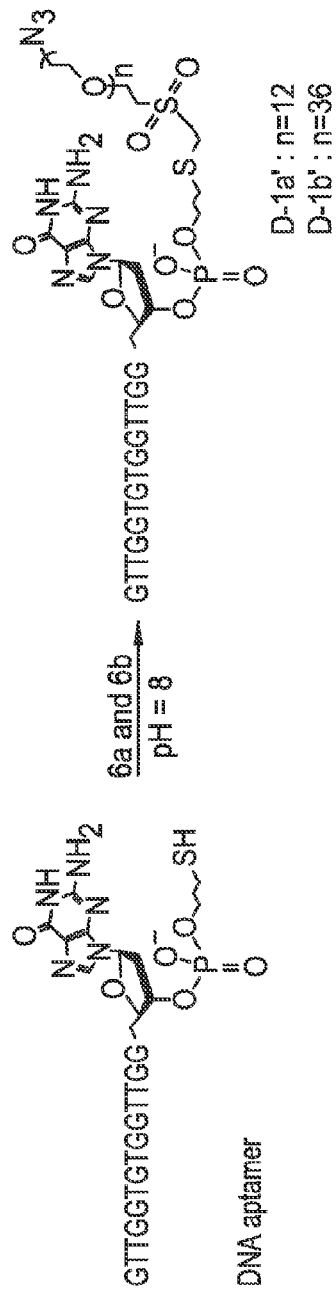
FIG. 11 is an illustration depicting tethering of a molecular linker to an affinity molecule, including the synthesis of two derivatised anti-thrombin nucleic acid aptamers (D-1a' and D-1b') using linkers 6a and 6b in a Michael addition.

The molecular anchor (3) was synthesized simply by reacting APS (1) with 2-(cyclooct-2-yn-1-yloxy)acetic acid (2) in the presence of 1-ethyl-3-(3-dimethylaminopropyl) carbodiimide (EDC, FIG. 10). The desired product was separated as a white solid by silica gel chromatography with a yield of 60%. The molecular linker for RI (6a, FIG. 4) was synthesized starting from hexaethylene glycol. First, azido-$(CH_2CH_2O)_6$-Ts (4, Ts=tosyl) was synthesized in a multi-gram scale (Loiseau, F. A. et al. J. Org. Chem. 2004, 69, 639-647; Svedhem, S.; et al. J. Org. Chem. 2001, 66, 4494-4503). The azido-$(CH_2CH_2O)_{12}$—OH (5) was prepared in a 71% yield by reacting 4 with sodium hexaethylene glycoxide (3 times excess) that was generated in situ by treating hexaethylene glycol with sodium hydride. In presence of potassium t-butoxide, 5 reacted with divinyl sulfone to furnish the desired product 6a in a yield of 64%. In the same manner, the linker azido-$(CH_2CH_2O)_{36}$-vinyl sulfone (6b) was synthesized by reacting azido-dPEG®—alcohol with divinyl sulfone in a yield close to that of 6a (FIG. 5). These two products were characterized with FTIR, NMR, and mass spectroscopy. Although vinyl sulfones may react with azides in presence of $CuSO_4$ and sodium ascorbate, it was determined by NMR monitoring that 6a and 6b were stable both in its pure form and in chloroform at room temperature at least for two days. They have been stored at −78° C. already for one year and no degradation has been observed. Maleimide is another reactive group that is functionally similar to vinyl sulfone in bioconjugation, but it may be less amenable to coexisting with azide because a [3+2] cycloaddition could spontaneously take place between these two functions in some circumstances. In addition, maleimide can undergo the thiol exchanges and ring hydrolysis (above pH 8), which may complicate outcomes of the conjugating reaction. Thus, vinyl sulfone was chosen as a Michael addition receptor of thiols in this attachment chemistry.

Figure 6:
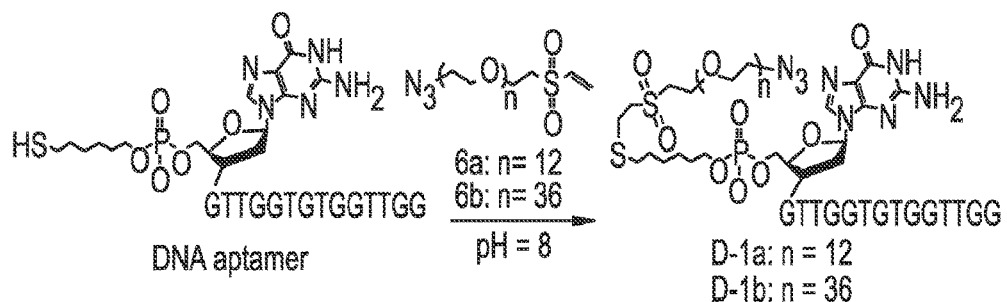
FIG. 6 is an illustration of a scheme to attach a molecular linker to anti-thrombin nucleic acid aptamer through Michael addition of thiol to vinyl sulfone.

Example 12: Synthesis in FIGS. 6 and 7

Figure 7:
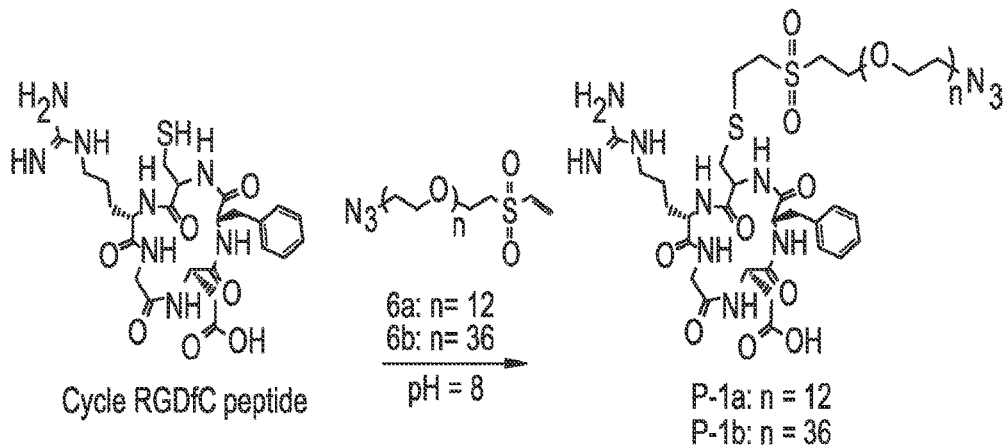
FIG. 7 is an illustration of a scheme to attach a molecular linker to a cyclic RGDfC peptide through Michael addition of thiol to vinyl sulfone.
Figure 8:
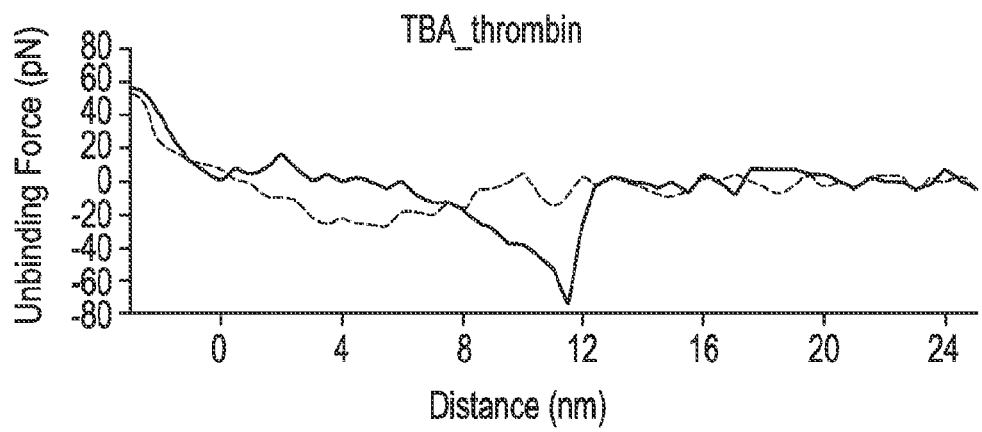
FIG. 8 is a graph depicting AFM force spectra of a thrombin binding aptamer (TBA) interacting with a thrombin (only retraction part shown) in which the solid line was taken from using a TBA functionalized tip against thrombin proteins immobilized on a mica surface, dotted line from after blocking the TBA tip with thrombin.
Figure 9:
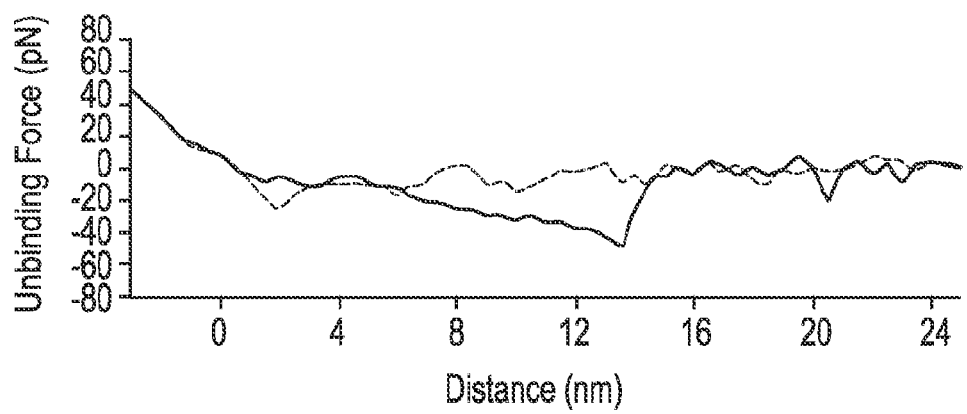
FIG. 9 is a graph depicting AFM force spectra of RGD interacting $\alpha_5\beta_1$ integrin proteins, in which the solid line was taken from using an RGDfC functionalized tip against $\alpha_5\beta_1$ integrin proteins immobilized on a mica surface; dotted line from after blocking the RGDfC tip with integrin.

Two affinity molecules, thrombin-binding DNA aptamer (TBA) and cyclic RGDfC peptide containing a RGD motif that binds to integrin receptors such as α5β1, were chosen to study the attachment chemistry. First, the disulfide at the 3'-end of the DNA aptamer from custom synthesis was reduced to thiol by tris(2-carboxyethyl)phosphine (TCEP) treatment, which then reacted with linker 6a and 6b at pH 8.0 in phosphate buffered aqueous solutions, respectively. Through the Michael addition of thiol to vinyl sulfone (FIG. 6), the DNA aptamer was converted to azido-PEGylated products D-1a with a 95% yield and D-1b with a 89% yield, based on HPLC analysis. The disulfide DNA was used as a negative control and it did not react with 6a and 6b, indicating that the vinyl sulfone is specific to thiol under the current conditions. The reaction between the vinyl sulfone and the thiolated DNA at pH 7-7.5 was very slow and did not complete even after one day. The thiol reaction is driven by the thiolate that is a much stronger nucleophile than its conjugate acid thiol. Since the alkyithiol is fairly acidic with pKa of about 10 to 11, the increase of pH may increase existence of the thiolate anion, resulting in an increased reaction rate. Under the similar conditions, the thiolated RGDfC was converted to products P-1a and P-1b quantitatively (FIG. 7). We did not observe side products by MALDI mass spectrometer and reverse phase HPLC analysis. In addition, time differences between reacting with 6a and 6b were not observed. These reactions were completed within three hours when starting with DNA or peptides in a range of millimolar concentrations.

Vinyl sulfone also reacts with alkyl amines under basic conditions. In these experiments, the amine functionalized aptamer and the cyclic RGDfK reacted with both 6a and 6b in phosphate buffered solutions at pH 8.8, but the reactions were very slow and not completed even after ten hours. With a well-tuned pH value, thus, the vinyl sulfone can specifically react with thiol in the presence of amino function.

Figure 13:
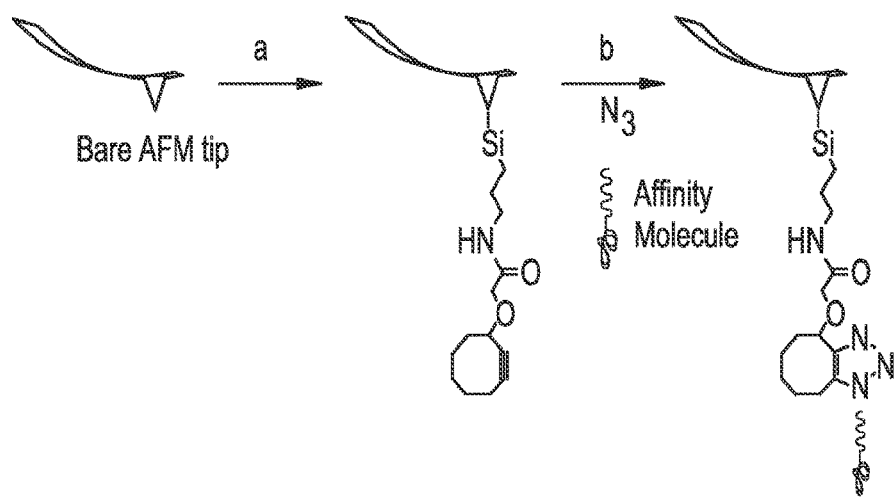
FIG. 13 is an illustration of a process of functionalizing an AFM tip with an affinity molecule, including the steps of: (a) coupling cyclooctyne to an AFM tip through silanization; (b) attaching affinity molecules to an AFM tip through alkyne-azide click reaction (only one regioisomeric product is drawn).
Figure 14A:
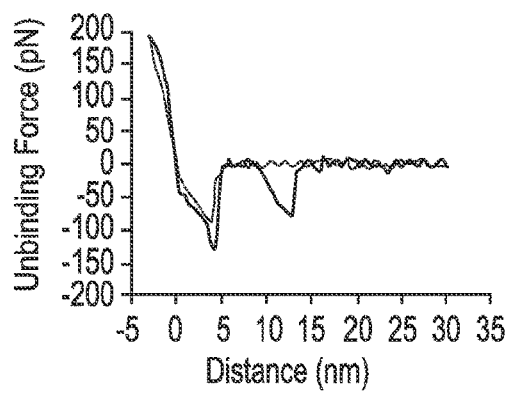
Figure 14B:
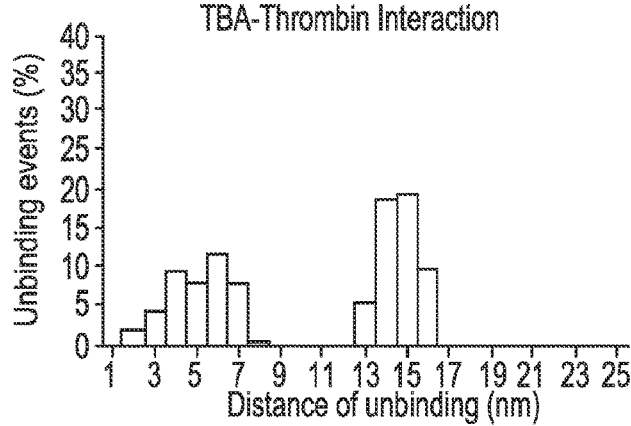
Figure 14C:
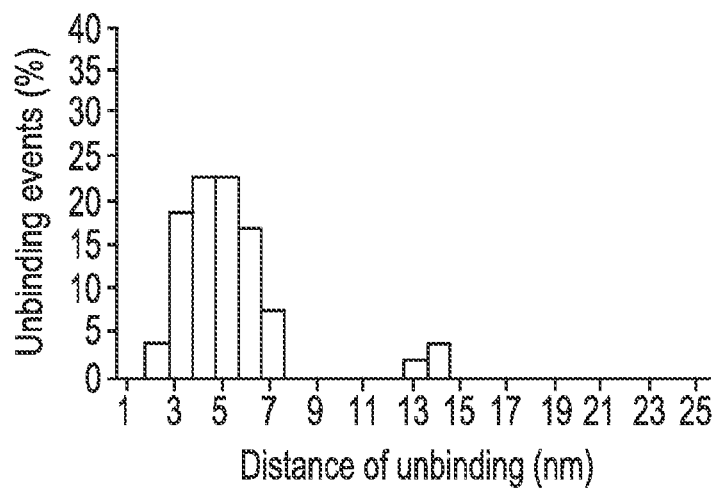
Figure 14D:
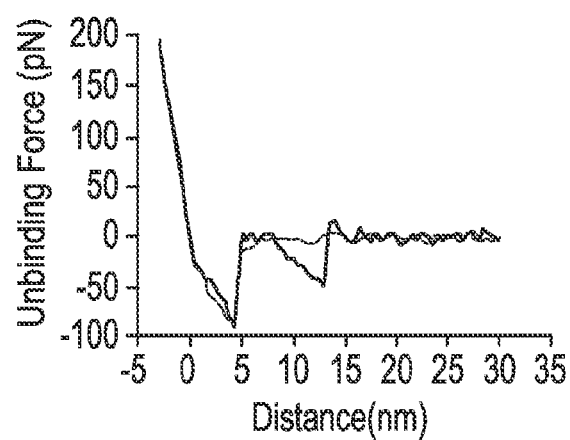

Example 13: Synthesis in FIGS. 12 and 13

To gain insight into the attachment chemistry of the disclosure, a pilot study was conducted on planar thermally oxidized silicon substrates, the surface of which may have a chemical reactivity similar to that of silicon AFM tips. It was found that compound 3 formed a monolayer with its physical properties close to those of the monolayer generated by reacting cyclooctynyloxy-acetic acid 2 with the APTES functionalized silicon substrate. As illustrated in FIG. 12, when APTES was deposited on a silicon oxide surface by chemical vapor deposition (route i-a), it changed the contact angle of water on the surface from 0° to ~46° (Table 1). The measured thickness of the organic layer was about 7.3 Å, slightly larger than the calculated distance from nitrogen to oxygen of APTES, indicating formation of a monolayer. Treating the APTES monolayer with compound 2 in the presence of EDC increased the contact angle to 76° and thickness to ~15.9 Å, close to the expected value. When the same silicon substrates were treated directly with an aqueous solution of compound 3 (route ii in FIG. 12), the measured contact angle and thickness were ~78° and 15.3 Å, respectively. This indicates that compound 3 may form a monolayer with a structure as suggested in S-3. In turn, the cyclooctyne surface was generated with a solution of fluorescent TBA containing an azide at its 3'-end and it became highly fluorescent after incubation for one hour, whereas the same surface treated with the fluorescent aptamer containing disulfide at the 3'-end (negative control) had negligible fluorescence (see FIG. 17). It has been confirmed that the azide functionalized TBA and cyclo-peptides reacted with the cyclooctyne effectively in the liquid phase (monitored by MALDI mass) before applying them to substrates or tips.

TABLE 1

Physical properties of surfaces derivatized with chemical functions

|  | Contact Angle (°) | Thickness (Å) |
| --- | --- | --- |
| S-2 (Route i-a) | 45.8 ± 0.9 | 7.3 ± 0.3 |
| S-3 (Route i-b) | 75.8 ± 0.8 | 15.9 ± 0.5 |
| S-3 (Route ii) | 77.9 ± 1.2 | 15.3 ± 0.3 |

A two-step protocol for the attachment was developed. As illustrated in FIG. 16, a bare AFM tip is first functionalized with the molecular anchor 3 in aqueous solution, followed by reacting with the azide functionalized affinity molecules under physiological conditions. It is worth noting that all of the reactions were carried out in aqueous solutions without using any of organic solvents (such as halogenated chloroform). The reaction between cyclooctyne and azide may yield two regioisomeric triazoles. Apparent regioisomeric effects on the following AFM measurements have not been observed. The attachment chemistry works well on two different AFM tip materials: SiN tipped probes (from Olympus and Bruker) and silicon probes (from NanoWorld). Before the chemical functionalization, these tips were cleaned sequentially with UV-ozone and oxygen plasma to increase the silanol density on the silicon surface for the silanization reaction.

Example 14: Validation of Attachment Chemistry Using Force Measurement

The attachment chemistry was validated using the functionalized SiN tips to measure forces of affinity molecules unbinding from their respective protein cognates. The protein sample was immobilized on APS-modified mica substrate using glutaraldehyde as a crosslinker (for procedure, see Wang, et al. Biophys. J. 2002, 83, 3619-3625). Initially, about 1000 force-distance curves were collected from each of measurement experiments with either D-1b against thrombin or P-1b against integrin $\alpha_5\beta_1$. The solid lines in Panel A and D of FIG. 14 show exemplary retracting force-distance curves used for data analysis, which accounts for more than one fourth of the collections. The selection was based on an assumption that a rupture directly related to unbinding of an affinity molecule from its protein cognate is likely to take place around the distance corresponding to the stretched length of a PEG linker (~13.5 nm in this instance). A distance histogram was created from each data set (Panel B and E of FIG. 14). They showed that the unbinding events were mainly distributed in the regions of 2-7 nm and 13-16 nm. Ratios of the rupture events between these two regions were 1:1.2 for the TBA tip against the thrombin protein and 1:1.3 for the RGD tip against the integrin protein respectively. After finishing the initial measurements, a thrombin or integrin solution was injected to the flow cell accordingly, and then another set of force curves were collected to determine the specificity of unbinding (see, for example, Lee, et al. Micron 2007, 38, 446-461). A disappearance of the specific unbinding ruptures from the force-distance curves was anticipated because the interactions of the affinity molecule tethered to the tip with its cognates on the substrate were blocked by protein from the solution. In fact, force-distance curves were obtained appearing like the dotted lines in Panel A and D of FIG. 14. Overall, the ruptures around the longer distances were reduced to a great extent and those around the shorter distances remained (Panel C and F of FIG. 14) in comparison with those prior to blocking. The rupture ratios between these two regions were changed to 12.3:1 for the TBA tip against the thrombin modified surface and 12:1 for the RGD tip against the integrin modified surface. To best interpret these results, the ruptures occurring at the distance around ~13.5 nm were assigned as specific unbinding of the affinity molecule from its protein cognates and those at shorter distances as nonspecific unbinding in Panel B and E of FIG. 17.

Figure 15A:
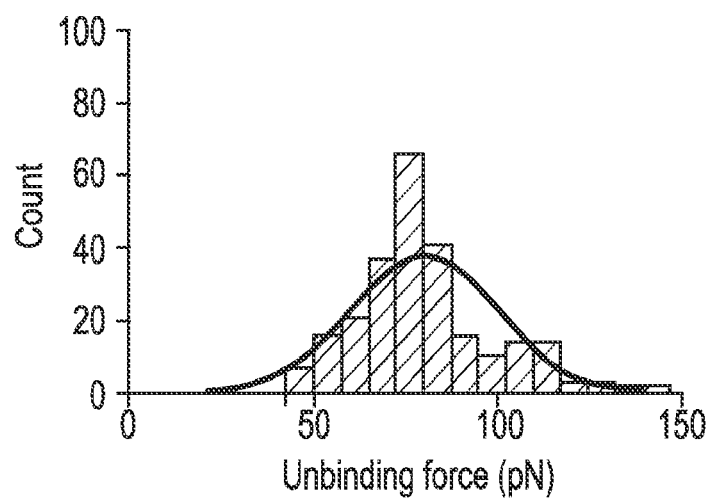
FIGS. 15A-B is a pair of graphs depicting (A) A force histogram of TBA unbinding from thrombin immobilized on the mica surface; (B) A force histogram of RGD unbinding from integrin immobilized on the mica surface.
Figure 15B:
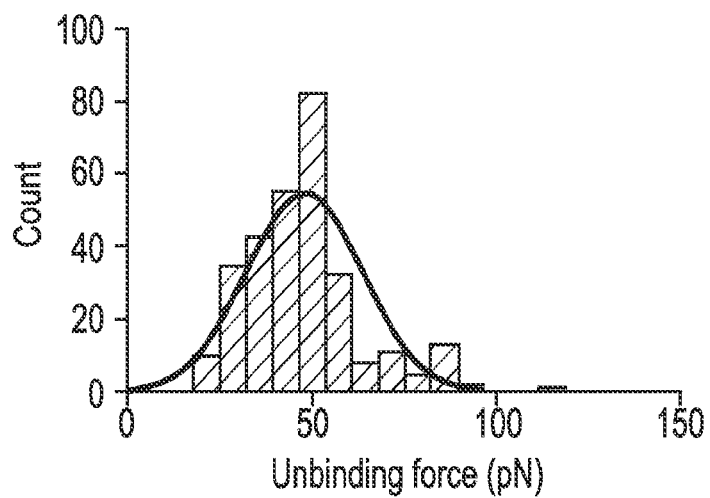
Figure 16A:
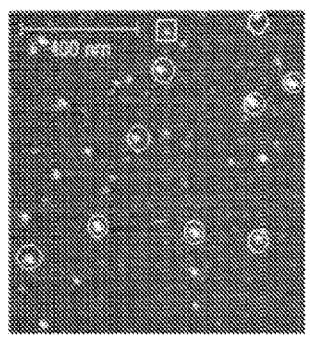
FIG. 16 is a series of recognition images depicting (A) Topographic image of thrombin proteins on mica; (B) Corresponding recognition image of A; (C) a recognition image taken after using a thrombin solution to block the TBA tip; (D) Topographic of integrin proteins on mica; (E) Corresponding recognition imaging of D; (F) a recognition image taken after using a integrin solution to block the RGD tip; (the circles in the images indicate those protein molecules that were recognized whereas the square indicates the protein that was not recognized.
Figure 16B:
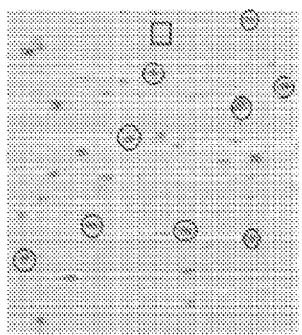
Figure 16C:
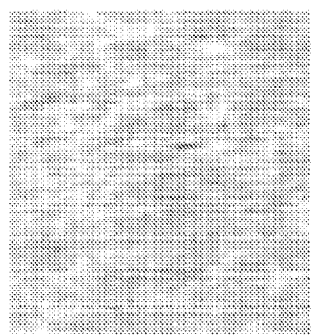
Figure 16D:
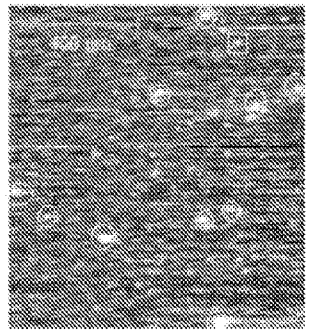
Figure 16E:
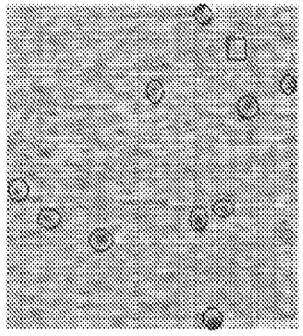
Figure 16F:
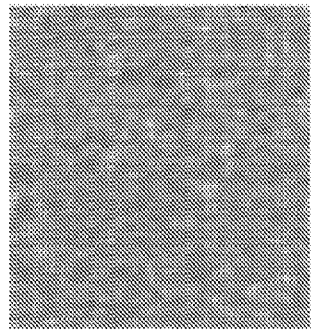

In total, there were 26.5% of force-distance curves containing the specific ruptures of TBA unbinding from thrombin in those initial ones. They were plotted as a force histogram and fitted into a Gaussian function, yielding a curve with the peak at ~80 piconewton (pN) (Panel A of FIG. 15). Similarly, 29.4% of the initial force-distance curves showed the specific unbinding ruptures for the RGD-integrin interactions, which results in a Gaussian curve with the peak at ~48 pN (Panel B of FIG. 15).

TABLE 2

Statistical data of functionalized AFM tips interacting with varied surfaces based on force-distance curves.

| On the tip | On the substrate | Unbinding events (%)* | Unbinding force (pN) |
| --- | --- | --- | --- |
| TBA | thrombin | 26.5 | 80.2 ± 34.5 |
| TBA (blocked) | thrombin | 7.0 | 15.6 ± 12.9 |
| TBA | BSA | 6.1 | 14.4 ± 9.4 |
| TBA | bare mica | 3.0 | 6.9 ± 3.8 |
| RGD | integrin | 29.4 | 48.0 ± 27.8 |
| RGD (blocked) | integrin | 6.7 | 11.1 ± 10.7 |

TABLE 2-continued

Statistical data of functionalized AFM tips interacting with varied surfaces based on force-distance curves.

| On the tip | On the substrate | Unbinding events (%)* | Unbinding force (pN) |
|---|---|---|---|
| RGD | BSA | 5.6 | 15.3 ± 14.4 |
| RGD | bare mica | 2.5 | 6.7 ± 4.0 |

*The percentage of ruptures taking place around the specific unbinding distance over total collected force curves.

Non-specific interactions between functionalized AFM tips with both bare and bovine serum albumin (BSA) immobilized mica substrates were examined. The results are given in Table 2. The functionalized AFM tips generally formed featureless force-distance curves on these surfaces. Only 6.1% of collected curves show unbinding ruptures from the nonspecific TBA-BSA interaction (median force 14.4 pN) and 5.6% from the nonspecific RGD-BSA interaction (median force 15.3 pN) around the expected distance, respectively. The functionalized tips interacted with the bare mica surfaces with even lower statistics and smaller unbinding forces. The non-specific unbinding forces that were measured were significantly smaller than those specific ones. These data demonstrate that the attachment chemistry of the disclosure has effectively tethered affinity molecules to AFM tips as well as maintained their specificity.

Example 15: Recognition Imaging (RI)

The AFM based recognition imaging is an effective tool for clinical diagnostics. The attachment and click chemistry of the disclosure works well in combination with the RI technique. Prior to this disclosure, the recognition imaging of clinically relevant proteins thrombin and integrin had not been reported. It has been demonstrated that a PEG linker with 12 units of ethyleneoxy ($CH_2CH_2O$) long can effectively produce quality recognition images. Linker 6a was tailored for RI. Its conjugate D-1a or P-1a was attached to Ni-coated MacMode tips (from Nanoworld) following the same protocol above mentioned. The protein samples (thrombin or $\alpha 5\beta 1$ integrin) were deposited on mica using the same glutaraldehyde chemistry. However, the optimal protein concentration (50 pg/μL in 1×PBS buffer, pH 7.4) for the RI was 20 times lower than that for the force measurements, which was pre-determined by imaging the surface with bare AFM tips in the air mode, ensuring that the protein molecules were well distributed in a predefined area. For one measurement, only 2-3 L of protein sample is needed in the current setup. Thus, a few femtomoles of proteins can readily be detected by the AFM based recognition imaging. FIG. 16 shows the images obtained from these RI experiments. RI simultaneously produces both topographic and recognition images. Each bright round spot in the topographic image represents a protein molecule (thrombin in Panel A and integrin in panel D of FIG. 16). This representation can be verified by examining the recognition images (Panel B and E of FIG. 16) where the dark spots represent recognition of those bright ones within the corresponding locations in the topographic image as expected protein molecules. About 77% recognition of thrombin and 84% recognition of integrin was obtained by comparison between their topography and recognition images. The recognition was further confirmed by the same blocking experiments as applied in the force measurements. After injecting a protein (thrombin or integrin) solution to the flow cell, most of the dark spots disappeared from the recognition images (Panel C and F of FIG. 16). These experiments demonstrate that the attachment chemistry of the disclosure is suitable for RI as well.

Example 16: Exemplary Procedure for Attaching an Affinity Molecule to an AFM Tip AFM tips (a batch of four or five) were first immersed in ethanol for five minutes, dried with ultrapure argon, and then treated with ultraviolet-ozone in a Boekel UV cleaner for 15 minutes and oxygen plasma (medium power) in a Harrick Plasma Cleaner for 2 minutes. These tips were immediately placed in a petri dish, to which an aqueous solution of compound 3 (50 mM) was added. After one hour, the tips were taken out, rinsed with water thrice, and dried gently with nitrogen.

In a humid surrounding, the cyclooctyne functionalized tips were placed in a petri dish and a solution of D-1a (50 μM, 20 μl) in 1×PBS buffer (pH 7.4) was added to cover all the tips, incubated at room temperature for one hour, and then the tips were rinsed thrice with the same buffer and used immediately. Other conjugates including D-1b, P-1a, and P-1b were also attached to the AFM tips under the exactly same conditions.

Example 17: Immobilization of Proteins on Mica Substrates

Freshly cleaved mica sheets (1.5×2.0 $cm^2$) were immersed in an aqueous solution of APS (50 mM). After one hour, the mica sheets were taken out and rinsed thoroughly with water thrice. In a humid surrounding, an aqueous solution of glutaraldehyde (1 mM, 200 μL) was added on the APS mica sheet. After 10 minutes, the mica substrates were rinsed with water thrice, and then a solution of protein in a 1×PBS buffer (3 μL) was placed on it, incubated for one hour, and rinsed with the 1×PBS buffer thrice. In general, protein concentrations were made around 10 ng/μL for force measurements and 0.05 ng/μL for recognition imaging. It should be noted that integrin we used was a lyophilized product from a solution containing: 0.26 mg/ml $\alpha 5\beta 1$, 20 mM Tris-HCl pH 7.5, 150 mM NaCl, 2 mM MgCl2, 0.2% Triton X-100, which was reconstituted by dissolving it in 1×PBS buffer.

Example 18: AFM Experimental Setup

An Agilent AFM 5500 (with inverted light microscope) system was used for the AFM experiments. Both force measurement and recognition imaging were carried out in 1×PBS buffer (pH 7.4). For force measurements, Veeco probes (Bicker, SiN tips) were used, having a force constant 0.05 N/m and a gold back coating, and the loading rate was 25000 pN/s.

For Recognition Imaging, magnetic cantilevers were used in AC (MAC) mode operation. Tips from NanoWorld were made of silicon and had a length of 125 m, width 35 μm and thickness 800 nm with force constant value of 0.14 N/m. Backsides of these tips were coated with 1 nm Ti/40 nm Ni. They have a remarkably low spread in force constant (a few percentage) and give stable MacMode operation in even quite reactive solution. Also, Olympus tips (silicon nitride, a force constant 0.08 N/m) were functionalized and used for few recognition experiments. Each of images was taken by scanning a 1×1 μm2 area.

For a blocking experiment, a protein solution (50 μL, 0.01 ng/μL in 1×PBS buffer, pH 7.4) was added to the flow cell, and the surface was imaged again. In general, a 15-20 minute waiting time is needed to effectively block the tip. The blocking for force measurements proceeded in the same way.

Example 19: Data Analysis

Topography images, recognition images and force spectra were recorded using Agilent PicoView software. The force-distance curves were analyzed in PicoView, and the corresponding unbinding forces were plotted in the form of histograms and fitted into the Gaussian function using MathWorks-MATLAB.

Other Embodiments

The patent and scientific literature (e.g., see below) referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, Manuscripts and scientific literature cited herein are hereby incorporated by reference.

While at least some embodiments have been described in conjunction with the detailed description thereof, the foregoing description is intended merely to illustrate some embodiments of the disclosure and not limit the scope of any inventions disclosed herein. It will be understood by those skilled in the art that various changes in form and details may be made therein without departing from the scope of any and all inventions supported by the present disclosure.

REFERENCES

Deshpande, P. S. White. *Expert Rev. Mol. Diagn.* 2012, 12, 645-659 (2012).
F. S. Ong, K. Das, J. Wang, H. Vakil. J. Z. Kuo, W.-L. B, Blackwell, S. W. Lim, M. O. Goodarzi. K. E. Bernstein, J. I. Rotter, W. W. Grody, *Expert Rev. Mol. Diagn.* 2012, 12, 593-602.
S. Ogino, C. S. Fuchs, E. Giovannucci, *Expert Rev. Mol. Diagn.* 2012, 12, 621-628.
Zieba, K. Grannas, O. Soderberg, M. Gullberg, M. Nilsson, U. Landegren, *New biotechnology* 2012, 29, 634-640.
D. A. Giljohann, C. A. Mirkin, *Nature* 2009, 462, 461-464.
I. Archakov. Y. D. Ivanov, A. V. Lisitsa, V. G. Zgoda, *Proteomics* 2007, 7, 4-9.
H. Zhang, Q. Zhao, X. F. Li, X. C. Le, *The Analyst* 2007, 132, 724-737.
M. Hu, J. Yan, Y. He, H. Lu, L. Weng, S. Song, C. Fan, L. Wang, *ACS nano* 2010, 4, 488-494.
Q. Zhang, B. Zhao, J. Yan, S. Song, R. Min, C. Fan, *Anal Chem* 2011, 83, 9191-9196.
H. Li, W. Qiang, M. Vuki, D. Xu, H. Y. Chen, *Anal Chem* 2011, 83, 8945-8952; (e) J. He, D. L. Evers, T. J. O'Leary, J. T. Mason, *Journal of nanobiotechnology* 2012, 10, 26.
J. Foote, H. N. Eisent, *Proc. Natl. Acad. Sci. USA* 1995, 92, 1254-1256.
S. K. Grebe, R. J. Singh, *Clin Biochem Rev* 2011, 32, 5-31.
Ruppen-Canas, P. P. Lopez-Casas, F. Garcia, P. Ximenez-Embun, M. Munoz, M. P. Morelli, F. X. Real, A. Senna, M. Hidalgo, K. Ashman, *Proteomics* 2012, 12, 1319-1327.
T. Shi, T. L. Fillmore, X. Sun, R. Zhao, A. A. Schepmoes, M. Hossain, F. Xie, S. Wu, J. S. Kim. N. Jones, R. J. Moore, L. Pasa-Tolic, J. Kagan, K. D. Rodland, T. Liu, K. Tang, D. G. Camp, 2nd, R. D. Smith, W. J. Qian, *Proceedings of the National Academy of Sciences of the United States of America* 2012, 109, 15395-15400.
D. M. Rissin, C. W. Kan. T. G. Campbell, S. C. Howes, D. R. Fournier, L. Song. T. Piech, P. P. Patel, L. Chang, A. J. Rivnak, E. P. Ferrell, J. D. Randall, G. K. Provuncher, D. R. Walt, D. C. Duffy, *Nat Biotechnol* 2010, 28, 595-599.
H. G. Hansma. *Annu. Rev. Phys. Chem.* 2001, 52, 71-92.
E. Oroudjev, S. Danielsen, H. G. Hansma, in *Nanobiotechnology—Concepts, Applications and Perspectives* (Eds.: C. M. Niemeyer, C. A. Mirkin), John Wiley & Sons 2004, pp. 387-403.
R. J. Heinisch, P. N. Lipke, A. Beaussart, S. E. K. Chatel, V. Dupres, D. Alsteens, Y. F. Dufrene, *Journal of Cell Science* 2012, 125, 1-7.
D. J. Muller, J. Helenius, D. Alsteens, Y. F. Dufrene, *Nat Chem Biol* 2009, 5, 383-390.
S. Ramachandran, F. Teran Arce, R. Lal, *Wiley interdisciplinary reviews. Systems biology and medicine* 2011, 3, 702-716.
V. Safenkova, A. V. Zherdev, B. B. Dzantievf, *Biochemistry* 2012, 77, 1536-1552; (g) X. Shi, X. Zhang, T. Xia, X. Fang, *Nanomedicine* (2012) 7(10), 2012, 7, 1625-1637; hL. B. Oddershede, *nature Chemical Biology* 2012, 8, 879-886.
E.-L. Lorin, V. i. T. Moy, H. Gaub, *Science* 1994, 264, 415-417.
U. Dammer, M. Hegner, D. Anselmetti, P. Wagner, M. Dreier, W. Huber, H.-J. Guntherodt, *Biophysical Journal* 1996, 70, 2437-2441.
P. F. Luckham, K. Smith, *Faraday Discussions* 1999, 111, 307-320.
S. ALLEN, J. DAVIES, M. C. DAVIES, A. C. DAWKES, C. J. ROBERTS, S. J. B. TENDLER, P. M. WILLIAMS, *Biochem. J.* 1999, 341, 173-178.
R. Avci, M. Schweitzer, R. D. Boyd, J. Wittmeyer, A. Steele, J. Toporski, I. Beech, F. T. Arce, B. Spangler, K. M. Cole, D. S. McKay, *Langmuir: the ACS journal of surfaces and colloids* 2004, 20, 11053-11063.
T. Tanaka, T. Sasaki, Y. Amemiya, H. Takeyama, S. Chow, T. Matsunaga, *Anal Chim Acta* 2006, 561, 150-155.
G. Neuert, C. Albrecht, E. Pamir, H. E. Gaub, *FEBS letters* 2006, 580, 505-509.
F. A. Carvalho, S. Connell, G. Miltenberger-Miltenyi, S. n. V. Pereira, A. Tavares, R. A. S. A. ns, N. C. Santos, *ACS Nano* 2010, 4, 4609-4620.
Meng, E. Paetzell, A. Bogorad, W. O. Soboyejo, *Journal of Applied Physics* 2010, 107, 114301.
S. Zapotoczny, R. Biedron, J. Marcinkiewicz, M. Nowakowska, *Journal of molecular recognition: JMR* 2012, 25, 82-88.
Y. J. Jung. J. A. Albrecht, J. W. Kwak. J. W. Park, *Nucleic Acids Res* 2012, 40, 11728-11736.
R. Zhu, S. Howorka, J. Proll, F. Kienberger, J. Preiner, J. Hesse, A. Ebner, V. P. Pastushenko, H. J. Gruber, P. Hinterdorfer, *Nature Nanotechnology* 2010, 5, 788-791.
Raab. W. Han, D. Badt, S. J. Smith-Gill, S. M. Lindsay, H. Schindler, P. Hinterdorfer. *Nature Biotechnology* 1999, 17, 902-905.
Stroh, H. Wang, R. Bash, B. Ashcroft, J. Nelson, H. Gruber. D. Lohr, S. M. Lindsay, P. Hinterdorfer, *Proceedings of the National Academy of Sciences of the United States of America* 2004, 101, 12503-12507.
F. Kienberger. A. Ebner, H. J. Gruber, P. Hinterdorfer, *Acc. Chem. Res.* 2006, 39, 29-36.

Lin, H. Wang, Y. Liu. H. Yan, S. Lindsay, *Biophys J* 2006, 90, 4236-4238.

H. Wang, Y. Dalal, S. Henikoff, S. Lindsay, *Epigenetics & chlrmatin* 2008, 1, 10.

A. Chtcheglova, P. Hinterdorfer, J. Mol. Recognit. 2011, 24, 788-794; (g) R. Creasey, S. Sharma, C. T. Gibson, J. E. Craig, A. Ebner, T. Becker. P. Hinterdorfer, N. H. Voelcker, *Ultramicroscopy* 2011, III, 1055-1061

Wang, C. Guo, M. Zhang, B. Park, B. Xu, *J. Phys. Chem. B* 2012, 116, 5316-5322.

P. Hinterdorfer. F. Kienberger. A. Raab, H. J. Gruber, W. Baumgartner, G. Kada, C. Riener, S. Wielert-Badt, C. Borken, H. Schindler, *Single Mol.* 2002, 1 99-103.

K. Riener, C. M. Stroh, A. Ebner, C. Klampfl, A. A. Gall, C. Romanin, Y. L. Lyubchenko, P. Hinterdorfer, H. J. Gruber, *Anal Chim Acta* 2003, 479, 59-75.

P. Hinterdorfer. H. J. Gruber, F. Kienberger, G. Kada, C. Riener, C. Borken, H. Schindler, *Colloids and Surfaces B: Biointerfaces* 2002, 23, 115-123.

Ebner, L. Wildling, A. S. M. Kamruzzahan, C. Rankl, J. r. Wruss, C. D. Hahn, M. Ho"lzl, R. Zhu, F. Kienberger, D. Blaas. P. Hinterdorfer. H. J. Gruber, *Bioconjugate Chem.* 2007, 18, 1176-1184.

Bruker, Application Note #130; eA. Ebner, P. Hinterdorfer, H. J. Gruber, *Ultramicroscopy* 2007, 107, 922-927; (f) E. Jauvert. E. Daguc, M. Séverac, L. Ressier. A.-M. Caminade, J.-P. Majoral, E. Trévisiol, *Sensors and Actuators B: Chemical* 2012, 168, 436-441.

W. T. Johnson, Application Note, Agilent Technologies.

S. M. Kamruzzahan, A. Ebner, L. Wildling, F. Kienberger, C. K. Riener, C. D. Hahn, P. D. Pollheimer, P. Winklehrer, M. Ho"lzl, B. Lackner, D. M. Scho"rkl, P. Hinterdorfer. H. J. Gruber. *Bioconjugate Chem.* 2006, 17, 1473-1481.

G. Li, N. Xi, D. H. Wang. *Proceedings of* 2005 *5th IEEE Conference on Nanotechnology* 2005; (j) A. P. Limanskii, *Biophysics* 2006, 51, 186-195.

K. Riener, F. Kienberger, C. D. Halm, G. M. Buchinger, I. 0. C. Egwim, T. Haselgrübler, A. Ebner, C. Romanin, C. Klampfl, B. Lackner, H. Prinz, D. Blaas, P. Hinterdorfer, H. J. Gruber, *Anal Chim Acta* 2003, 497, 101-114.

Wildling. B. Unterauer. R. Zhu, A. Rupprecht, T. Haselgrubler, C. Rankl, A. Ebner, D. Vater, P. Pollheimer, E. E. Pohl, P. Hinterdorfer, H. J. Gruber, *Bioconjug Chem* 2011, 22, 1239-1248.

P. Limansky, L. S. Shlyakhtenko, S. Schaus, E. Henderson, Y. L. Lyubchenko, *Probe Microscopy* 2002, 2, 227-234.

T. Vandenberg, L. Bertilsson, B. Liedberg, K. Uvdal, R. Erlandsson, H. Elwing, I. Lundstrom, *Journal of Colloid and Interface Science* 1991, 147, 103-118.

S. Guha Thakurta. A. Subramanian, *Colloids and Surfaces A: Physicochemnrical and Engineering Aspects* 2012, 414, 384-392.

S. Shlyakhtenko, A. A. Gall, A. Filonov, Z. Cerovac, A. Lushnikov, Y. L. Lyubchenko. *Ultramicroscopy* 2003, 97, 279-287.

Y. L. Lyubchenko, L. S. Shlyakhtenko, A. A. Gall, *Methods in Molecular Biology* 2008, 543, 337-351.

cY. L. Lyubchenko, L. S. Shlyakhtenko, *Methods* 2009, 47, 206-213.

Y. L. Lyubchenko, L. S. Shlyakhtenko, T. Ando, *Methods* 2011, 54, 274-283.

What is claimed is:

1. A compound of Formula I:

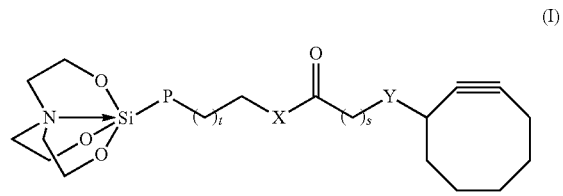

wherein:
X is O, $CH_2$, NH or $NCH_3$;
Y is O, $CH_2$, NH or $NCH_3$;
P is $CH_2$ or O; and
s and t are each independently 0, 1, 2, 3, 4, or 5.

2. The compound of claim 1, wherein the compound is

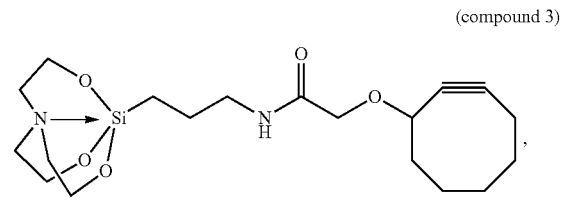 [SMILES: O=C(COC1C#CCCCCC1)NCCC[Si]12OCCN(CCO1)CCO2]

(compound 3)

3. A compound of Formula III:

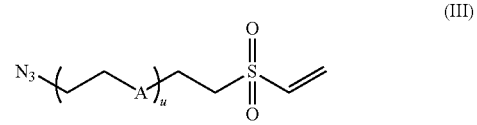

(III)

wherein:
A is $CH_2$ or O; and
u is any integer ranging from 1 to 36.

4. The compound of claim 3, wherein A is O.
5. The compound of claim 3, wherein u is 12.
6. The compound of claim 3, wherein the compound is a compound of Formula IV:

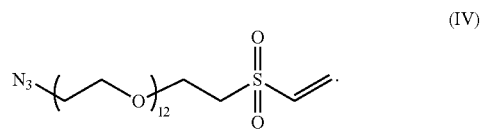

(IV)

7. A composition comprising

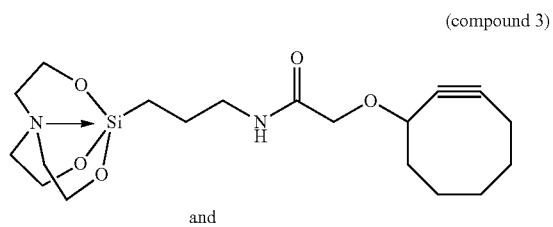

(compound 3)

and

-continued

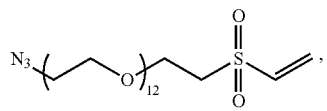
(IV)

8. A method for preparing a compound according to Formula I, comprising contacting a silatrane to a functionalized acid in the presence of a coupling reagent.

9. The method of claim 8, further comprising an organic solvent.

10. The method of claim 8, where the organic solvent is dichloromethane.

11. The method of claim 8, wherein the silatrane is 1-(3-aminopropyl)silatrane (APS).

12. The method of claim 8, wherein the functionalized acid is 2-(cyclooct-2-yn-1-yloxy)acetic acid.

13. The method of claim 8, wherein the coupling agent is 1-ethyl-3-(3-dimethylaminopropyl)carbodiimide (EDC).

14. The method of claim 8, wherein the compound of Formula I is (compound 3)

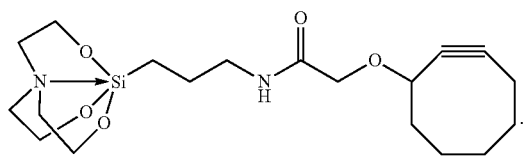

15. A method of preparing compound 6a, comprising:
a. mixing hexatheylene glycol and (compound 4)

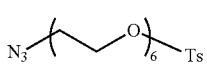

in the presence of a first base to form (compound 5)

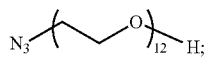

and
b. mixing divinyl sulfone, (compound 5)

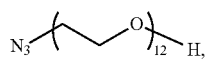

and a second base, to form (compound 6a)

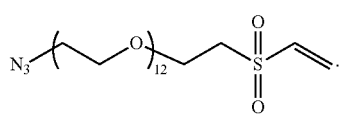
6a

16. The method of claim 15, wherein the first base is sodium hydride.

17. The method of claim 15, wherein the second base is a tert-butoxide.

18. The method of claim 17, wherein the tert-butoxide is potassium tert-butoxide.

19. A method for preparing immobilized affinity molecules attached to a functionalized AFM tip, comprising a step of mixing AFM tip with a compound of claim 1.

20. A method of functionalizing an AFM tip, comprising reacting the silatrane moiety of a compound of claim 1 with silanol on the surface of the AFM tip.

* * * * *